(12) United States Patent
Xu et al.

(10) Patent No.: US 11,465,986 B2
(45) Date of Patent: Oct. 11, 2022

(54) CRYSTAL FORM OF C-MET INHIBITOR AND SALT FORM THEREOF AND PREPARATION METHOD THEREFOR

(71) Applicant: FUJIAN AKEYLINK BIOTECHNOLOGY CO., LTD., Fujian (CN)

(72) Inventors: Xiongbin Xu, Shanghai (CN); Gang Li, Shanghai (CN); Ting Yao, Shanghai (CN); Kun Wang, Shanghai (CN); Lihong Hu, Shanghai (CN); Charles Z. Ding, Shanghai (CN)

(73) Assignee: FUJIAN AKEYLINK BIOTECHNOLOGY CO., LTD., Fujian (CN)

( * ) Notice: Subject to any disclaimer, the term of this patent is extended or adjusted under 35 U.S.C. 154(b) by 67 days.

(21) Appl. No.: 17/049,579

(22) PCT Filed: Apr. 26, 2019

(86) PCT No.: PCT/CN2019/084515
§ 371 (c)(1),
(2) Date: Oct. 22, 2020

(87) PCT Pub. No.: WO2019/206268
PCT Pub. Date: Oct. 31, 2019

(65) Prior Publication Data
US 2021/0238163 A1 Aug. 5, 2021

(30) Foreign Application Priority Data

Apr. 26, 2018 (CN) .......................... 201810387693.2

(51) Int. Cl.
| | |
|---|---|
| *C07D 401/14* | (2006.01) |
| *A61P 35/00* | (2006.01) |
| *A61K 31/435* | (2006.01) |
| *A61K 31/4412* | (2006.01) |
| *A61K 31/444* | (2006.01) |
| *A61K 31/505* | (2006.01) |
| *A61K 31/506* | (2006.01) |

(52) U.S. Cl.
CPC ............ *C07D 401/14* (2013.01); *A61P 35/00* (2018.01); *C07B 2200/13* (2013.01)

(58) Field of Classification Search
CPC ... C07D 401/14; A61P 35/00; C07B 2200/13; A61K 31/435; A61K 31/4412; A61K 31/444; A61K 31/505; A61K 31/506
See application file for complete search history.

(56) References Cited

U.S. PATENT DOCUMENTS

| | | |
|---|---|---|
| 2007/0208046 A1 | 9/2007 | Otake et al. |
| 2010/0197690 A1 | 8/2010 | Schadt et al. |
| 2011/0257181 A1 | 10/2011 | Stieber et al. |
| 2011/0269767 A1 | 11/2011 | Becker et al. |
| 2019/0248763 A1 | 8/2019 | Xu et al. |

FOREIGN PATENT DOCUMENTS

| | | |
|---|---|---|
| CN | 1930126 A | 3/2007 |
| CN | 101743241 A | 6/2010 |
| CN | 102264727 A | 11/2011 |
| TW | 200906409 A | 2/2009 |
| TW | 201029655 A | 8/2010 |
| WO | 2010072296 A1 | 7/2010 |
| WO | 2010078897 A1 | 7/2010 |
| WO | 2018077227 A1 | 5/2018 |

OTHER PUBLICATIONS

Golub, T. R., "Molecular classification of cancer: class discovery and class prediction by gene expression monitoring." Science 286.5439 (1999): 531-537.*
Christensen, J. G., "A selective small molecule inhibitor of c-Met kinase inhibits c-Met-dependent phenotypes in vitro and exhibits cytoreductive antitumor activity in vivo." Cancer research 63.21 (2003): 7345-7355.*
Humbert, M., "Cytoprotective autophagy is involved in resistance towards MET inhibitors in human gastric adenocarcinoma cells." (2012): 1909-1909.*
Medová, M.,"The novel ATP-competitive inhibitor of the MET hepatocyte growth factor receptor EMD1214063 displays inhibitory activity against selected MET-mutated variants." Molecular cancer therapeutics 12.11 (2013): 2415-2424.*
Sawyers, C., "Targeted cancer therapy." Nature 432.7015 (2004): 294-297.*
Sep. 2, 2010 International Search Report issued in International Patent Application No. PCT/CN2010/073565.
Dorsch Dieter et al. Identification and optimization of pyridazinones as potent and selective c-Met kinase inhibitors, Feb. 16, 2015.
Mino R Caira Ed "Crystalline Polymorphism of Organic Compounds", Feb. 26, 1999.

(Continued)

*Primary Examiner* — John M Mauro
(74) *Attorney, Agent, or Firm* — Houston Beshining Law Office PLLC; Liangang Ye

(57) ABSTRACT

Disclosed are a crystal form of a c-MET inhibitor and a salt form thereof and a preparation method therefor. Specifically involved are the compound as shown in formula (I), and a salt form and a crystal form thereof, and also included is the use of the crystal form and the salt form in the preparation of medicines for treating cancers.

(I)

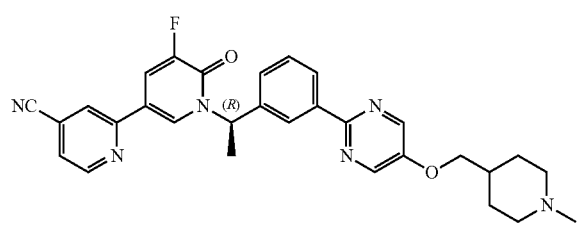

16 Claims, 5 Drawing Sheets

(56) References Cited

OTHER PUBLICATIONS

Hilfiker, R. et al. "Relevance of Solid-state Properties for Pharmaceutical Products" Jan. 2006.
Nov. 9, 2021 First Office Action issued in Japanese application No. 2020-560239.
Dec. 7, 2021 First Office Action issued in Korean application No. 10-2020-7033747.
Dec. 6, 2021 First Office Action issued in Taiwan application No. 108114732.
Unpublished priority CN 2018103876932.
Aug. 8, 2019 International Search Report issued in International Patent Application No. PCT/CN2019/084515.
Aug. 8, 2019 Written Opinion of the International Searching Authority issued in International Patent Application No. PCT/CN2019/084515.
Feb. 8, 2022 Japanese Second Office Action issued in Japanese Patent Application No. 2020-560239.
Apr. 19, 2022 European Office Action issued in European Patent Application No. 19791723.0

* cited by examiner

CRYSTAL FORM OF C-MET INHIBITOR AND SALT FORM THEREOF AND PREPARATION METHOD THEREFOR

The present application is a National Stage of International Application No. PCT/CN2019/084515, filed on Apr. 26, 2019, which claims the benefit of Chinese patent application CN201810387693.2 filed on Apr. 26, 2018. The contents of the Chinese patent application are incorporated herein by reference in their entireties.

TECHNICAL FIELD

The present application relates to a crystal form of a c-MFT inhibitor, a salt form thereof and a preparation method therefor, and a use of the crystal form and the salt form in the manufacture of a medicament for treating a tumor is also included in the present application.

BACKGROUND

The c-Met encoded by proto-oncogene Met is a receptor tyrosine kinase with high affinity belonging to RON subgroup. It is the only known receptor for scattering factor or hepatocyte growth factor (HGF). HGF induces phosphorylation of c-Met by binding to its extracellular domain, and recruits a variety of interstitial factors such as GAB1 (growth factor receptor binding protein-1) and GAB2 (growth factor receptor binding protein-2) in the C-terminal multifunctional domain, further attracting molecules such as SHP2, PI3K to bind here, hence activating RAS/MAPK, PI3K/AKT, JAK/STAT pathways etc., thereby regulating the growth, migration, proliferation and survival of cells. Abnormal action of the c-Met pathway would lead to tumorigenesis and metastasis, and abnormal high expression of c-Met has been found in various human malignancies such as bladder cancer, gastric cancer, lung cancer and breast cancer.

In addition, c-Met is also associated with drug resistance to multiple kinase inhibitors in tumors. The interaction between c-Met and various membrane receptors (crosstalk) constitutes a complex network system. The crosstalk between c-Met and adhesion receptor CD44 amplifies the response of signal peptide; the crosstalk between c-Met and the brain protein receptor activates c-Met level of independent ligand HGF, and then enhances the invasion effect; the crosstalk between c-Met and the pro-apoptotic receptor FAS accelerates apoptosis; the crosstalk between c-Met and various receptor tyrosine kinases such as EGFR, VEGFR regulates the activation between each other, thus affecting the angiogenesis process. The crosstalk between c-Met and these membrane receptors promotes tumorigenesis, metastasis and induces drug resistance.

There are currently two kinds of anti-tumor drugs targeting at c-Met pathway: one is monoclonal antibody against HGF or c-Met; the other is small molecule inhibitor against c-Met. The small molecule inhibitors that have already entered clinical research or under research include PF-2341066, EMD-1214063, XL-184 and ARQ-197 etc. Among them, Tepot nib has the best anti-tumor activity and has a strong inhibitory effect on a variety of tumor cells overexpressing c-Met (activity on c-MET enzyme $IC_{50}$=3.67 nM, on MHCC97-H cells $IC_{50}$=6.2 nM), and it has entered clinical research phase II. However, although tepotinib has high selectivity, it still has the drawbacks of low metabolic stability and high clearance rate in vivo. Therefore, metabolically stable c-Met inhibitors are urgently needed to compensate for the deficiency.

CONTENT OF THE PRESENT INVENTION

The present disclosure provides a crystal form A of a compound represented by formula (I), wherein the X-ray powder diffraction pattern thereof comprises characteristic diffraction peaks at the following angle 2θ: 4.54°±0.2°, 13.70°±0.2°, 17.84±0.2°, 21.24°±0.2° and 26.62±0.2°.

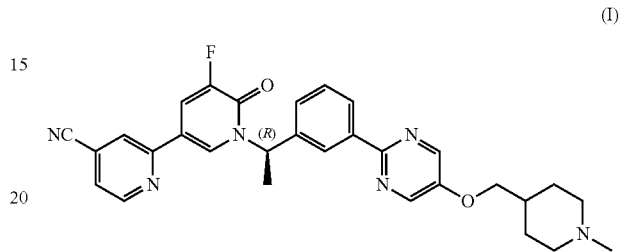

(I)

In some embodiments of the present disclosure, the X-ray powder diffraction pattern of the crystal form A comprises characteristic diffraction peaks at the following angle 2θ: 4.54°±0.2®, 13.70°±0.2°, 15.14±0.2°, 17.84±0.2°, 18.40°±0.2°, 21.24°±0.2®, 24.06°±0.2°, 26.62±0.2° and 27.44±0.2°.

In some embodiments of the present disclosure, the X-ray powder diffraction pattern of the crystal form A is as shown in FIG. 1.

In some embodiments of the present disclosure, the X-ray powder diffraction pattern of the crystal form A comprises characteristic diffraction peaks at the following angle 2θ: 4.538°, 9.021°, 11.300°, 13.699°, 15.141°, 16.640°, 17.840°, 18.399°, 19.039°, 19.620°, 20.441°, 21.241°, 22.598°, 24.060°, 24.962°, 25.660° 26.621°, 27.440°, 28.258°, 29.159°, 31.081°, 32.465°, 34.780°, 35.400°, 36.920° and 38.760°.

In some embodiments of the present disclosure, the analytical data of the X-ray powder diffraction pattern of the crystal form A is as shown in Table 1.

TABLE 1

Analytical data of the XRPD pattern of the crystal form A of the compound represented by formula (I)

| No. | 2θ Angle (°) | d-spacing (Å) | Relative intensity (%) |
|---|---|---|---|
| 1 | 4.538 | 19.4556 | 100 |
| 2 | 9.021 | 9.7948 | 57.2 |
| 3 | 11.300 | 7.8240 | 27.4 |
| 4 | 13.699 | 6.4587 | 97.2 |
| 5 | 15.141 | 5.8467 | 68.5 |
| 6 | 16.640 | 5.3233 | 40.6 |
| 7 | 17.840 | 4.9679 | 72.6 |
| 8 | 18.399 | 4.8181 | 68.8 |
| 9 | 19.039 | 4.6576 | 55.8 |
| 10 | 19.620 | 4.5210 | 32.1 |
| 11 | 20.441 | 4.3412 | 26.7 |
| 12 | 21.241 | 4.1796 | 74.7 |
| 13 | 22.598 | 3.9314 | 23.1 |
| 14 | 24.060 | 3.6958 | 68.4 |
| 15 | 24.962 | 3.5643 | 16.0 |
| 16 | 25.660 | 3.4688 | 13.3 |
| 17 | 26.621 | 3.3459 | 95.9 |
| 18 | 27.440 | 3.2478 | 66.2 |

TABLE 1-continued

Analytical data of the XRPD pattern of the crystal
form A of the compound represented by formula (I)

| No. | 2θ Angle (°) | d-spacing (Å) | Relative intensity (%) |
|---|---|---|---|
| 19 | 28.258 | 3.1556 | 16.6 |
| 20 | 29.159 | 3.0601 | 20.2 |
| 21 | 31.081 | 2.8751 | 18.4 |
| 22 | 32.465 | 2.7556 | 1.5 |
| 23 | 34.780 | 2.5773 | 14.7 |
| 24 | 35.400 | 2.5336 | 9.5 |
| 25 | 36.920 | 2.4327 | 6.5 |
| 26 | 38.760 | 2.3214 | 12.1 |

In some embodiments of the present disclosure, the crystal form A can also be characterized by a DSC pattern having an onset temperature of 171.90° C. and a peak temperature of 173.09° C.

In some embodiments of the present disclosure, the differential scanning calorimetry curve of the crystal form A has an endothermic peak at 171.90° C.±3° C.

In some embodiments of the present disclosure, the differential scanning calorimetry curve of the crystal form A is as shown in FIG. 2.

In some embodiments of the present disclosure, the crystal form A can be characterized by a TGA pattern showing a weight loss of 0.1870% occurred at 223.23° C., a further weight loss of 10.03% occurred at 305.06° C., and a large weight loss occurred after 205.06° C.

In some embodiments of the present disclosure, the thermogravimetric analysis curve of the crystal form A shows a weight loss of 0.1870% occurred at 223.23° C.±3° C., and a weight loss of 10.22% occurred at 305.06° C.±3° C.

In some embodiments of the present disclosure, the thermogravimetric analysis curve of the crystal form A is as shown in FIG. 3.

In some embodiments of the present disclosure, the infrared spectrogram of the crystal form A has characteristic absorption peaks at 3046 cm$^{-1}$±5 cm$^{-1}$, 2938 cm$^{-1}$±5 cm$^{-1}$, 2914 cm$^{-1}$±5 cm$^{-1}$, 2884 cm$^{-1}$±5 cm$^{-1}$, 2849 cm$^{-1}$±5 cm$^{-1}$, 2780 cm$^{-1}$±5 cm$^{-1}$, 2734 cm$^{-1}$1±5 cm$^{-1}$, 2679 cm$^{-1}$±5 cm$^{-1}$, 7242 cm$^{-1}$±5 cm$^{-1}$, 1732 cm$^{-1}$±2 cm$^{-1}$, 1716 cm$^{-1}$±2 cm$^{-1}$, 1671 cm$^{-1}$±2 cm$^{-1}$, 1631 cm$^{-1}$±2 cm$^{-1}$, 1595 cm$^{-1}$±2 cm$^{-1}$, 1556 cm$^{-1}$±2 cm$^{-1}$, 1547 cm$^{-1}$±2 cm$^{-1}$, 1507 cm$^{-1}$±2 cm$^{-1}$, 1482 cm$^{-1}$±2 cm$^{-1}$, 1387 cm$^{-1}$±7 cm$^{-1}$, 1070 cm$^{-1}$±2 cm$^{-1}$ and 1196 cm$^{-1}$±2 cm$^{-1}$.

The present disclosure also provides a compound represented by formula (II).

The present disclosure also provides a crystal form B of the compound represented by formula (II), wherein the X-ray powder diffraction pattern thereof comprises characteristic diffraction peaks at the following angle 2θ: 4.34°±0.2°, 12.99°±0.2°, 15.35°±0.2° and 25.50°±0.2°.

In some embodiments of the present disclosure, the X-ray powder diffraction pattern of the crystal form B comprises characteristic diffraction peaks at the following angle 2θ: 4.34° 10.2°, 6.50°±0.2°, 8.65°±0.2°, 10.82°±0.2°, 12.99°±0.2°, 15.35°±0.2°, 17.96°±0.2° and 25.50°±0.2°.

In some embodiments of the present disclosure, the X-ray powder diffraction pattern of the crystal faun B is as shown in FIG. 4.

In some embodiments of the present disclosure, the X-ray powder diffraction pattern of the crystal form B comprises characteristic diffraction peaks at the following angle 2θ: 4.335°, 6.502°, 8.645°, 10.816° 12.986°, 15.349°, 15.782°, 16.109°, 17.955°, 18.447°, 19.057°, 19.534°, 19.816°, 20.531°, 21.16°, 22.265°, 22.752°, 23.907°, 24.407°, 25.499°, 26.248°, 26.886°, 27.725°, 28.004°, 28.653°, 29.127°, 29.779°, 30.432°, 31.064°, 33.734° and 37.02°.

In some embodiments of the present disclosure, the analytical data of the X-ray powder diffraction pattern of the crystal form B is as shown in Table 2.

TABLE 2

Analytical data of the XRPD pattern of the crystal
form B of the compound represented by formula (II)

| No. | 2θ Angle (°) | d-spacing (Å) | Relative intensity (%) |
|---|---|---|---|
| 1 | 4.335 | 20.367 | 100 |
| 2 | 6.502 | 13.5825 | 44 |
| 3 | 8.645 | 10.2196 | 54.7 |
| 4 | 10.816 | 8.1731 | 34.4 |
| 5 | 12.986 | 6.8119 | 96.2 |
| 6 | 15.349 | 5.7678 | 58.4 |
| 7 | 15.782 | 5.6105 | 23.5 |
| 8 | 16.109 | 5.4974 | 9.9 |

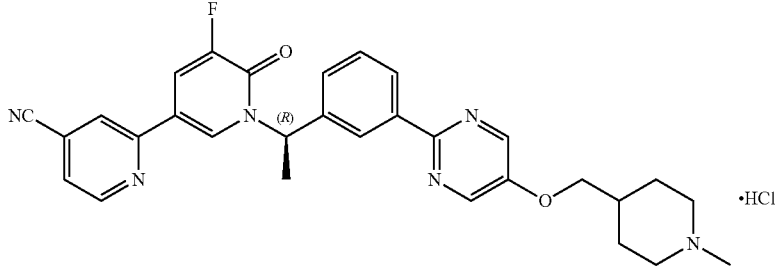

(II)

TABLE 2-continued

Analytical data of the XRPD pattern of the crystal form B of the compound represented by formula (II)

| No. | 2θ Angle (°) | d-spacing (Å) | Relative intensity (%) |
|---|---|---|---|
| 9 | 17.955 | 4.9361 | 51.3 |
| 10 | 18.447 | 4.8056 | 23.3 |
| 11 | 19.057 | 4.6533 | 21.8 |
| 12 | 19.534 | 4.5406 | 38.3 |
| 13 | 19.816 | 4.4767 | 33.3 |
| 14 | 20.531 | 4.3224 | 5.1 |
| 15 | 21.16 | 4.1953 | 19 |
| 16 | 22.265 | 3.9895 | 49.9 |
| 17 | 22.752 | 3.9052 | 6.8 |
| 18 | 23.907 | 3.7191 | 8.3 |
| 19 | 24.407 | 3.644 | 5.3 |
| 20 | 25.499 | 3.4903 | 71.4 |
| 21 | 26.248 | 3.3924 | 8.9 |
| 22 | 26.886 | 3.3133 | 21 |
| 23 | 27.725 | 3.2149 | 13.8 |
| 24 | 28.004 | 3.1836 | 11.2 |
| 25 | 28.653 | 3.1129 | 22.9 |
| 26 | 29.127 | 3.0633 | 16.6 |
| 27 | 29.779 | 2.9977 | 5.6 |
| 28 | 30.432 | 2.9348 | 14.5 |
| 29 | 31.064 | 2.8766 | 11.6 |
| 30 | 33.734 | 2.6548 | 6.1 |
| 31 | 37.02 | 2.4263 | 4.7 |

In some embodiments of the present disclosure, the differential scanning calorimetry curve of the crystal form B has endothermic peaks at 43.98° C.±3° C. and 219.64° C.±3° C.

In some embodiments of the present disclosure, the differential scanning calorimetry curve of the crystal form B is as shown in FIG. 5.

In some embodiments of the present disclosure, the thermogravimetric analysis curve of the crystal form B shows a weight loss of 0.5270% occurred at 73.64° C.±3° C., and a weight loss of 1.542% occurred at 230.90° C.±3° C.

In some embodiments of the present disclosure, the thermogravimetric analysis curve of the crystal form B is as shown in FIG. 6.

The present disclosure also provides a compound represented by formula (III).

The present disclosure also provides a crystal form C of the compound represented by formula (III), wherein the X-ray powder diffraction pattern thereof comprises characteristic diffraction peaks at the following angle 2θ: 6.94°±0.2°, 19.08°±0.2°, 21.05°±0.2° and 24.73°±0.2°.

In some embodiments of the present disclosure, the X-ray powder diffraction pattern of the crystal form C comprises characteristic diffraction peaks at the following angle 2θ: 6.94°±0.2°, 9.94°±0.2°, 17.29°±0.2°, 18.04°±0.2°, 19.08°±0.2°, 21.05°±0.2°, 24.12°±0.2° and 24.73°±0.2°.

In some embodiments of the present disclosure, the X-ray powder diffraction pattern of the crystal form C is as shown in FIG. 7.

In some embodiments of the present disclosure, the X-ray powder diffraction pattern of the crystal form C comprises characteristic diffraction peaks at the following angle 2θ: 6.94°, 9.94°, 13.36°, 15.271°, 16.83°, 17.286°, 18.038°, 18.767°, 19.082°, 20.605°, 21.054°, 21.884°, 22.615°, 23.228°, 24.118°, 24.728°, 25.182°, 25.813°, 28.182°, 30.757°, 31.498°, 33.318°, 33.77° and 34.595°.

In some embodiments of the present disclosure, the analytical data of the X-ray powder diffraction pattern of the crystal form C is as shown in Table 3.

TABLE 3

Analytical data of the XRPD pattern of the crystal form C of the compound represented by formula (III)

| No. | 2θ Angle (°) | d-spacing (Å) | Relative intensity (%) |
|---|---|---|---|
| 1 | 6.94 | 12.7261 | 100 |
| 2 | 9.94 | 8.8916 | 43.5 |
| 3 | 13.36 | 6.6218 | 20.6 |
| 4 | 15.271 | 5.7972 | 16.9 |
| 5 | 16.83 | 5.2636 | 18.7 |
| 6 | 17.286 | 5.1258 | 47.6 |
| 7 | 18.038 | 4.9136 | 49 |
| 8 | 18.767 | 4.7244 | 35.5 |
| 9 | 19.082 | 4.6471 | 67.4 |
| 10 | 20.605 | 4.3069 | 9.3 |
| 11 | 21.054 | 4.216 | 52 |
| 12 | 21.884 | 4.058 | 5.5 |
| 13 | 22.615 | 3.9285 | 8.8 |
| 14 | 23.228 | 3.8263 | 25.7 |
| 15 | 24.118 | 3.687 | 33.7 |
| 16 | 24.728 | 3.5974 | 53.8 |
| 17 | 25.182 | 3.5335 | 28.4 |

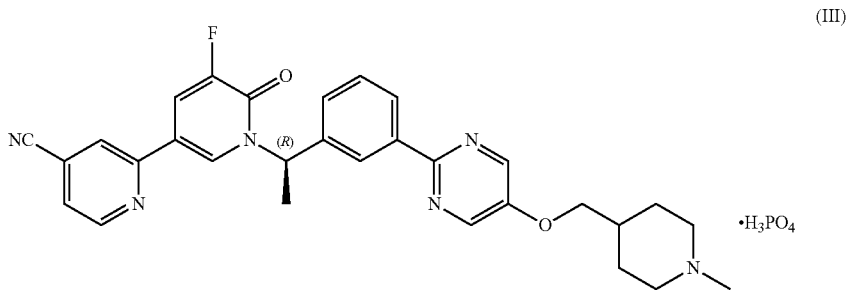

(III)

·H₃PO₄

TABLE 3-continued

Analytical data of the XRPD pattern of the crystal form C of the compound represented by formula (III)

| No. | 2θ Angle (°) | d-spacing (Å) | Relative intensity (%) |
|---|---|---|---|
| 18 | 25.813 | 3.4485 | 17 |
| 19 | 28.182 | 3.1638 | 12.3 |
| 20 | 30.757 | 2.9046 | 5.3 |
| 21 | 31.498 | 2.838 | 7.3 |
| 22 | 33.318 | 2.687 | 3.3 |
| 23 | 33.77 | 2.652 | 6.4 |
| 24 | 34.595 | 2.5907 | 8.7 |

In some embodiments of the present disclosure, the differential scanning calorimetry curve of the crystal form C has an endothermic peak at 198.16° C.±3° C.

In some embodiments of the present disclosure, the differential scanning calorimetry curve of the crystal form C is as shown in FIG. 8.

In some embodiments of the present disclosure, the thermogravimetric analysis curve of the crystal form C shows a weight loss of 0.4541% occurred at 204.73° C.±3° C.

In some embodiments of the present disclosure, the thermogravimetric analysis curve of the crystal form C is as shown in FIG. 9.

The present disclosure also provides a use of the compounds or the crystal forms in the manufacture of a medicament for treating cancer.

The present disclosure also provides the compounds or the crystal forms for treating cancer.

The present disclosure also provides a method of treating cancer by administering the compounds or the crystal forms.

In the present disclosure, the term cancer is preferably liver cancer.

Technical Effect

The preparation process of the salt forms and crystal forms of the compound represented by formula (I) of the present disclosure is simple, and the crystal forms are relatively stable when subjected to high temperature and high humidity, and is convenient for producing preparations.

Definitions and Explanations

Unless otherwise indicated, the following terms and phrases used in this document are intended to have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The intermediate compounds of the present disclosure can be prepared by various synthetic methods known to those skilled in the art, including the embodiments described below, the embodiments formed by combining the embodiments described below with other chemical synthesis methods, and equivalent alternatives well-known for those skilled in the art. Preferred embodiments include, but are not limited to, the embodiments of the present disclosure.

The chemical reactions in the embodiments of the present disclosure are carried out in a suitable solvent, and the solvent should be suitable for the chemical change, and the required reagents and materials of the present disclosure. In order to obtain the compounds of the present disclosure, it is sometimes necessary for those skilled in the art to modify or select the synthetic steps or reaction schemes based on the existing embodiments.

The present disclosure will be specifically described below by way of embodiments, but the scope of the present disclosure is not limited thereto.

All solvents used in the present disclosure are commercially available and can be directly used without further purification.

The present disclosure employs the following abbreviations:

(R)—CBS: (3aR)-1-methyl-3,3-diphenyl-3a,4,5,6-tetrahydropyrrolo[1,2-c][1,3,2]oxazaborole;

DIEA: N,N-diisopropylethylamine;

DMF: NN-dimethylformamide;

THF: tetrahydrofuran;

Pd(dppf)Cl$_2$: [1,1'-bis(diphenylphosphino)ferrocene]palladium dichloride;

Pd(PPh$_3$)$_2$Cl$_2$: bis(triphenylphosphine)palladium dichloride.

Compounds are named manually or by ChemDraw® software, and the commercially available compounds use their vendor directory names.

The analysis method for X-ray powder diffractometer (XRPD) in the present disclosure Instrument model: Bruker D8 Advance X-ray diffractometer Detection method: about 10-20 mg of the sample was used for XRPD detection.

The detailed XRPD parameters were as follows:

X-ray tube: Cu, kα, (λ=1.54056 Å).

X-ray tube voltage: 40 kV, X-ray tube current: 40 mA

Divergence slit: 0.60 mm

Detector slit: 10.50 mm

Anti-scattering slit: 7.10 mm

Scanning range: 3 or 4-40 deg

Step size: 0.02 deg

Step time: 0.12 second

Rotation speed of sample tray: 15 rpm

The method for Differential Scanning calorimeter (DSC) in the present disclosure Instrument Model: TADSCQ2000 differential scanning calorimeter Detection method: 0.5-1 mg of the sample was placed in a DSC aluminum crucible for testing, under the condition of 50 mL/min N$_2$ at a heating rate of 10° C./min, the sample was heated from room temperature (25° C.) to 300° C., or 350° C.

The method for Thermal Gravimetric Analyzer (TGA) in the present disclosure

Instrument Model: TAQ5000 thermal gravimetric analyzer

Detection method: 2-5 mg of the sample was placed in a TGA platinum crucible for testing, under the condition of 25 mL/min N$_2$ at a heating rate of 10° C./min, the sample was heated from room temperature (25° C.) to 300° C., 350° C. or until a weight loss of 20%.

The Dynamic Vapor Sorption Analyzer (DVS)

Instrument Model: DVSAdvantage-1 (SMS)

Detection condition: about 10-15 mg of the sample was used for DVS detection.

Equilibrium: dm/dt=0.01%/min: (time: 10 min, longest: 180 min)

Drying: 0% RH, 120 min

RH (%) gradient for testing: 10%

RH (%) gradient range for testing: 0%-90%-0%

The hygroscopicity was evaluated using the scales in the following Table 4:

TABLE 4

Scales for hygroscopicity

| Scales for hygroscopicity | Hygroscopic weight gain* |
|---|---|
| Deliquescence | Absorbing sufficient water to form liquid |
| High hygroscopicity | ΔW % ≥ 15% |
| Medium hygroscopicity | 15% > ΔW % ≥ 2% |
| Low hygroscopicity | 2% > ΔW % ≥ 0.2% |
| No or almost no hygroscopicity | ΔW % < 0.2% |

*Hygroscopic weight gain at 25° C./80% RH

The method for High Performance Liquid Chromatograph (HPLC) in the present disclosure Instrument Model: Agilent 1200 High Performance Liquid Chromatograph The analysis method is as follows:

TABLE 5

HPLC analysis method for related substance content test

| Instrument | Agilent 1200 High Performance Liquid Chromatograph |
|---|---|
| Column | Ascentis Express C18, 4.6 × 150 mm, 2.7 μm (94#) |
| Mobile phase A | 0.1% phosphoric acid aqueous solution |
| Mobile phase B | Acetonitrile solution |
| Flow rate | 1.0 mL/min |
| Injection volume | 5.0 μL |
| Detection wavelength | 220 nm/272 nm |
| Column temperature | 40° C. |
| Diluent | 3/1 (v/v) Acetonitrile:pure water |

| | duration (min) | Mobile phase A (%) | Mobile phase B (%) |
|---|---|---|---|
| Gradient elution program | 0.00 | 95 | 5 |
| | 14.00 | 70 | 30 |
| | 20.00 | 65 | 35 |

TABLE 5-continued

HPLC analysis method for related substance content test

| | | |
|---|---|---|
| 25.00 | 30 | 70 |
| 28.00 | 10 | 90 |
| 33.00 | 10 | 90 |
| 33.01 | 95 | 5 |
| 38.00 | 95 | 5 |

DETAILED DESCRIPTION OF THE EMBODIMENT

Figure 1:
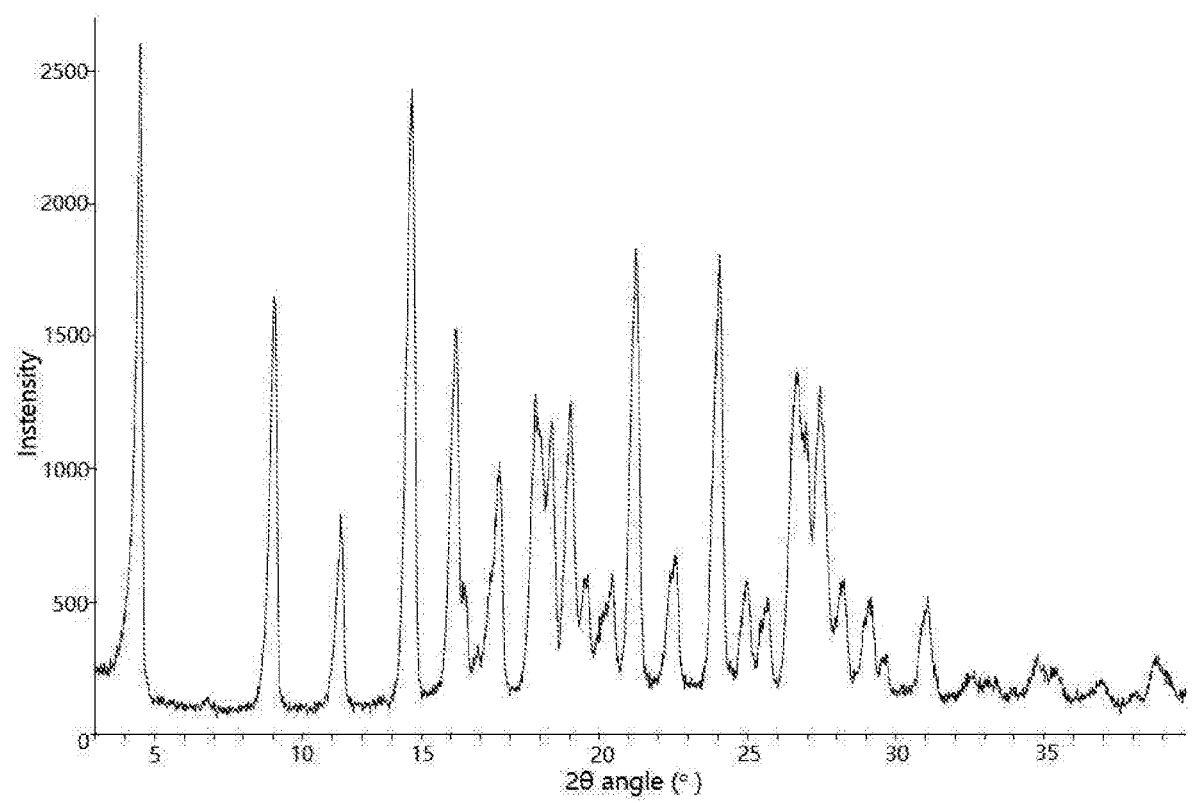
FIG. 1 is the XRPD spectrum of the crystal form A of the compound represented by formula (I).

In order to better understand the contents of the present disclosure, the following embodiments further illustrate the present disclosure, but the present disclosure is not limited thereto.

Embodiment 1: Preparation of the Crystal Form A of the Compound Represented by

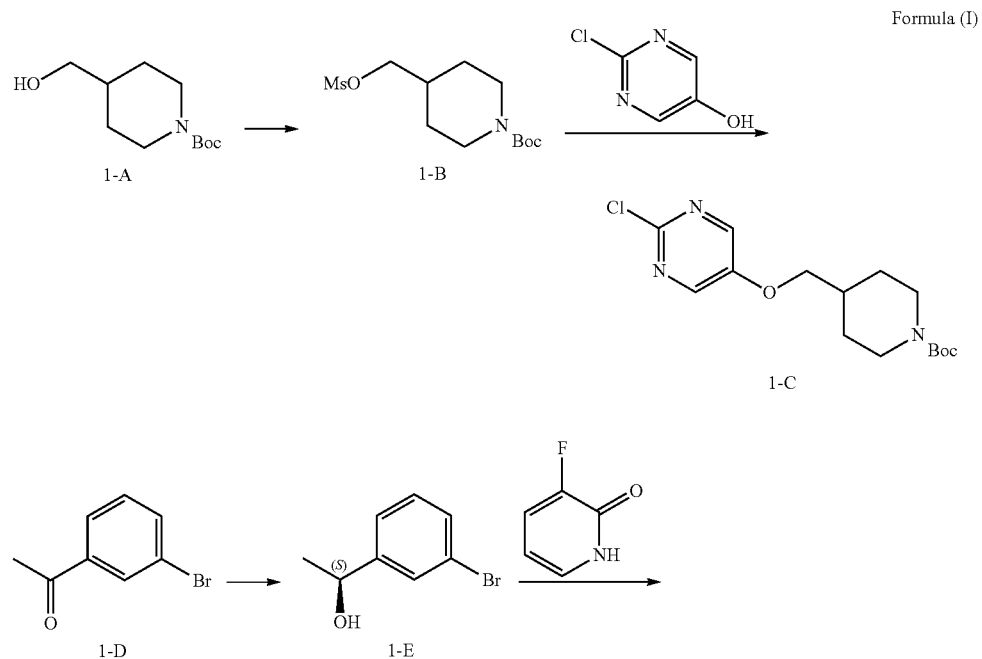

-continued
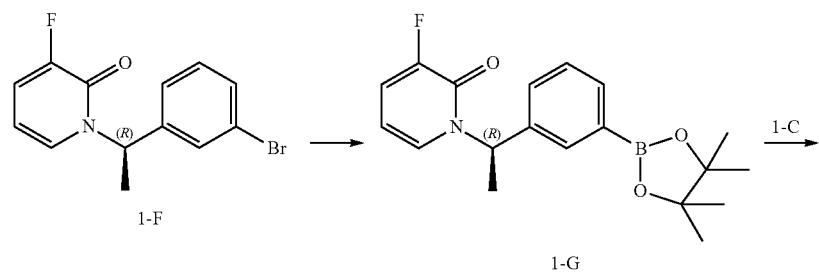
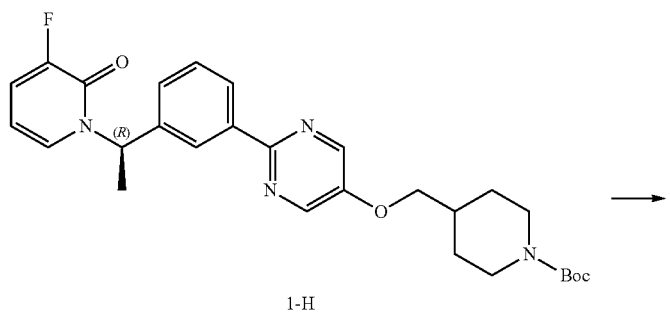
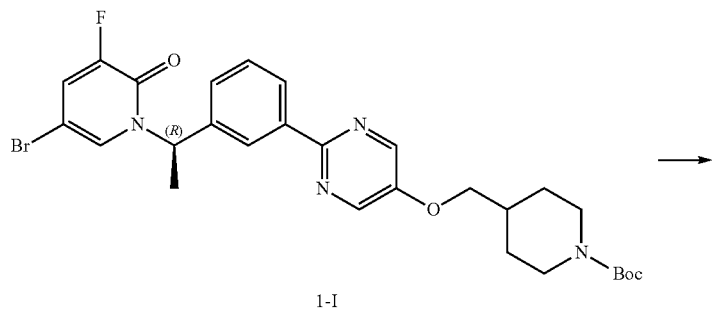
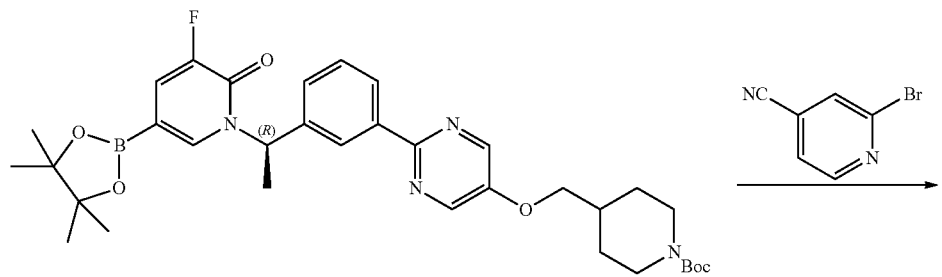
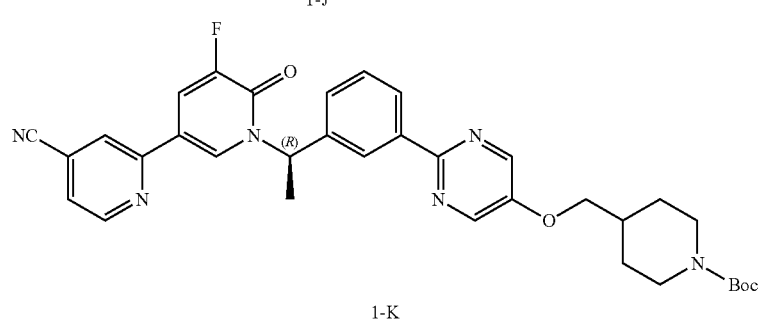

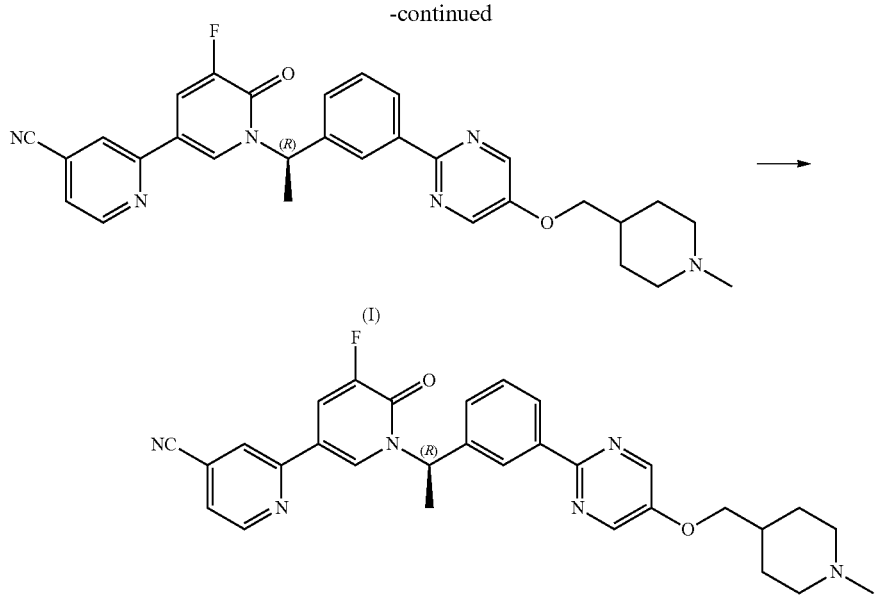

Crystal form A of (I)

Preparation of 1-B:

Under nitrogen atmosphere at −30° C., diisopropylethylamine (2.9 kg, 22.67 mol) and methanesulfonyl chloride (2.2 kg, 19.51 mol) were added dropwise to a solution of compound 1-A (4 kg, 25.19 mol) in dichloromethane (20 L) while stirring. After the addition was complete, the mixture was stirred at −10° C. for 1 hour. LCMS detected the completion of the reaction. The reaction solution was washed with saturated ammonium chloride solution (12 L*2), dried over anhydrous sodium sulfate, filtered and concentrated to give intermediate 1-B, which was directly used in the next step without further purification. LCMS (ESI) m/z: 316.0 [M+Na]$^+$ Preparation of 1-C:

Under nitrogen atmosphere, potassium carbonate (1.54 kg, 11.15 mol) was added to a solution of intermediate 1-B (5.45 kg, 18.58 mol) and 2-chloropyrimidin-5-ol (2.42 kg, 18.56 mol) in DMF (25 L). The reaction was carried out at 90° C. for 16 hours, LCMS detected the completion of the reaction. The reaction mixture was poured into water (75 L) and stirred for 16 hours and then filtered. The filter cake was added to water (20 L) and stirred for 16 hours, filtered, and the filter cake was then dried to give the intermediate 1-C. LCMS (ESI) m/z: 328.1 [M+H]$^+$; $^1$HNMR (400 MHz, CDCl$_3$) δ ppm 1.21-1.36 (m, 2H) 1.44-1.49 (m, 9H) 1.81 (br d, J=12.10 Hz, 2H) 1.91-2.08 (m, 1H) 2.75 (br t, J=11.98 Hz, 2H) 3.90 (d, J=6.24 Hz, 2H) 4.01-4.37 (m, 2H) 8.28 (s, 2H).

Preparation of 1-E:

Under nitrogen atmosphere at −30° C., a solution of compound 1-D (5 kg, 25.19 mol) in tetrahydrofuran (5 L) was added to a mixed solution of (R)—CBS (12.5 L, 1 mol/L) and borane dimethyl sulfide (5 L, 10 mol/L). The reaction was carried out at −30° C. for 1 hour, and LCMS detected the completion of the reaction. Methanol (10 L) was added dropwise to the reaction solution to quench the reaction and then concentrated under reduced pressure. Ethyl acetate (2 L) and n-hexane (20) was added to the residue. After the dissolution of the residue, hydrochloric acid (10 L, 2 mol/L) was added and stirred for 1 hour, filtered, and the filtrate was washed with hydrochloric acid (12 L*3, 2 mol/L) and saturated brine (15 L). The organic layer was dried over anhydrous sodium sulfate, filtered, and concentrated to give the intermediate 1-E. $^1$HNMR (400 MHz, DMSO-d$_6$) δ ppm 1.31 (d, J=6.53 Hz, 3H), 4.61-4.84 (m, 1H), 5.30 (d, J=4.39 Hz, 1H), 7.25-7.31 (m, 1H), 7.31-7.37 (m, 1H), 7.41 (brd, J=7.65 Hz, 1H), 7.53 (s, 1H).

Preparation of 1-F:

Under nitrogen atmosphere, 3-fluoro-1H-pyridin-2-one (723.39 g, 6.4 mol), tri-n-butylphosphine (1.39 kg, 6.88 mol) and 1,1'-(azodicarbonyl)-dipiperidine (1.74 kg, 6.89 mol) were added sequentially into a solution of intermediate 1-E (1.2 kg, 5.97 mol) in toluene (30 L). The reaction solution was heated to 90° C. and the reaction was carried out for 2 hours, after which LCMS detected the completion of the reaction. The reaction solution was cooled to room temperature and centrifuged, the filtrate was washed with hydrochloric acid (9 L*2, 4 mol/L) and concentrated under reduced pressure. The residue was added to methyl tert-butyl ether (12 L). After the dissolution of the residue, the mixture was washed with hydrochloric acid (9 L*3, 4 mol/L) and saturated brine (9 L*2) separately. The organic phase was dried over anhydrous sodium sulfate, filtered and concentrated under reduced pressure. To the residue was added n-hexane (10 L) and the mixture was stirred for 16 hours, filtered. The filter cake was dried to give intermediate 1-F. LCMS (ESI) m/z: 297.9[M+H]$^+$; $^1$HNMR (400 MHz, DMSO-d$_6$) δ ppm 1.74 (d, J=7.09 Hz, 3H), 6.10 (td, J=7.24, 4.58 Hz, 1H), 6.46 (q, J=7.01 Hz, 1H), 6.95 (dt, J=7.09, 1.53 Hz, 1H), 7.08 (ddd, J=9.20, 7.43, 1.71 Hz, 1H), 7.22-7.32 (m, 2H), 7.43-7.53 (m, 2H).

Preparation of 1-G:

Under nitrogen atmosphere, a solution of intermediate 1-F (2 kg, 6.75 mol), bis(pinacolato)diboron (1.89 kg, 7.43 mol), bis(triphenylphosphine)palladium dichloride (48.51 g, 67.54 mmol) and potassium acetate (1.34 kg, 13.51 mol) in 1,4-dioxane (20 L) was heated to 90° C. and the reaction was carried out for 2 hours, after which LCMS detected the completion of the reaction. The reaction solution of compound 1-G was directly used in the next reaction without further treatment.

Preparation of 1-H:

Under nitrogen atmosphere, intermediate 1-C (2.44 kg, 7.43 mol), sodium carbonate (1.43 kg, 13.51 mol), Pd(dppf)Cl$_2$ (299.60 g, 405.22 mmol) and water (4 L) were sequentially added to the reaction solution of compound 1-G. The reaction solution was heated to 100° C. and the reaction was carried out for 16 hours. LCMS detected the completion of the reaction. The reaction solution was cooled to 80° C. and then filtered. Water (12 L) was added dropwise to the filtrate and stirred for 16 hours, then filtered. The filter cake was washed with water, dried and methyl ten-butyl ether (35 L) and acetone (1 L) were added thereto and stirred for 16 hours. The mixture was filtered, and the filter cake was collected and dried to give intermediate 1-H. LCMS (ESI) m/z: 531.1 [M+Na]$^+$; $^1$HNMR (400 MHz, DMSO-d$_6$) δ ppm 1.10-1.26 (m, 2H) 1.40 (s, 9H) 1.77 (brd, J=7.15 Hz, 5H) 1.97 (brd, J=3.64 Hz, 1H) 2.63-2.90 (m, 2H) 3.88-4.03 (m, 2H) 4.06 (d, J=6.40 Hz, 2H), 6.17-6.36 (m, 2H), 7.31-7.63 (m, 4H), 8.17-8.30 (m, 2H), 8.64 (s, 2H).

Preparation of 1-I:

Under nitrogen atmosphere at 30° C., 1,3-dibromo-5,5-dimethylimidazolin-2,4-dione (1 kg, 3.5 mol) was added to a solution of intermediate 1-H (2.63 kg, 5.17 mol) in DMF (27 L), the reaction was carried out at 30° C. for 1 hour, after which LCMS detected the completion of the reaction. Water (16.2 L) was added dropwise to the reaction solution and stirred for 16 hours, then filtered. The filter cake was washed with water and dried, and then added to acetone (17.6 L). The mixture was heated to reflux and stirred for 1 hour, then water (12 L) was added dropwise and stirred for 16 hours. The mixture was filtered, and the filter cake was dried to give intermediate 1-I. LCMS (ESI) m/z: 611.1 [M+Na]$^+$; $^1$HNMR (400 MHz, DMSO-d$_6$) δ ppm 1.10-1.27 (m, 2H), 1.40 (s, 9H), 1.71-1.87 (m, 5H), 1.93-2.06 (m, 1H), 2.67-2.85 (m, 2H), 3.99 (brd, J=11.67 Hz, 2H), 4.07 (brd, J=16.27 Hz, 2H), 6.23 (q, J=6.86 Hz, 1H), 7.42-7.57 (m, 2H), 7.71 (dd, J=9.29, 1.76 Hz, 1H), 7.85 (s, 1H), 8.18-8.30 (m, 2H), 8.65 (s, 2H).

Preparation of 1-J:

Under nitrogen atmosphere, a solution of intermediate 1-I (2.1 kg, 3.58 mol), bis(pinacolato)diboron (1.82 kg, 7.17 mol), tetrakis(triphenylphosphine)palladium (127.09 g, 110 mmol) and potassium acetate (719.68 g, 7.16 mol) in 1,2-dimethoxyethane (21 L) was heated to 85° C. and the reaction was carried out for 2 hours, after which LCMS detected the completion of the reaction. The reaction solution of compound 1-K was directly used in the next reaction without further treatment.

Preparation of 1-K:

Under nitrogen atmosphere, 2-bromopyridine-4-carbonitrile (707 g, 3.86 mol), sodium carbonate (741 g, 6.99 mol), tetrakis(triphenylphosphine)palladium (163 g, 141 mmol) and water (4.2 L) were added to the reaction solution of compound 1-J. The reaction solution was heated to 85° C. and the reaction was carried out for 16 hours. LCMS detected the completion of the reaction. After the reaction solution was cooled to 50° C., water (12.6 L) was added dropwise to the reaction solution and stirred for 16 hours, and then filtered. The filter cake was dried, and then slurried by addition of a mixed solvent of isopropanol:water=30:1 for 3 times. The solid was collected and dried to give intermediate 1-K. LCMS (ESI) m/z: 633.2 [M+Na]$^+$; $^1$HNMR (400 MHz, DMSO-d$_6$) δ ppm 1.09-1.26 (m, 2H), 1.40 (s, 9H), 1.76 (brd, J=11.17 Hz, 2H), 1.91 (d, J=7.1.5 Hz, 3H), 1.93-2.05 (m, 1H), 2.57-2.92 (m, 2H) 3.98 (brd, J=10.92 Hz, 2H), 4.05 (d, J=6.40 Hz, 2H), 6.35 (q, J=7.03 Hz, 1H), 7.47-7.56 (m, 2H), 7.73 (dd, J=5.02, 1.00 Hz, 1H), 8.19 (dd, J=11.29, 2.13 Hz, 1H), 8.22-8.27 (m, 1H), 8.30 (s, 1H), 8.40 (s, 1H), 8.48 (s, 1H), 8.64 (s, 2H), 8.79 (d, J=5.02 Hz, 1H).

Preparation of the Compound Represented by Formula (I):

Under nitrogen atmosphere, intermediate 1-K (2.4 kg, 3.93 mol) was added to a solution of methanesulfonic acid (758.66 g, 7.89 mol) in methanol (7.2 L) in batches, and the reaction solution was heated to 50° C. and stirred for 2 hours. LCMS detected the intermediate 1-K was completely consumed, and then methanol (16.8 L), sodium acetate (645.54 g, 7.87 mol), formaldehyde (639.63 g, 7.88 mol, 37% aqueous solution) and sodium triacetoxyborohydride (1.25 kg, 5.91 mol) were sequentially added to the reaction solution. The reaction mixture was stirred for 16 hours, and LCMS detected the completion of the reaction. The reaction mixture was filtered, ammonium hydroxide (3 L) and water (4.5 L) were added dropwise to the filtrate and stirred for 6 hours, and then filtered. The filter cake was washed with water and dried. The solid was added to tetrahydrofuran (13 L) and heated to 50° C. After the dissolution of the solid, thiourea resin (650 g) was added and stirred at 50° C. for 2 hours, filtered. Thiourea resin (650 g) was added to the filtrate and stirred at 50° C. for 2 hours, and then filtered. Thiourea resin (650 g) was added to the filtrate and stirred at 50° C. for 16 hours, and then filtered. Activated carbon powder (150 g) was added to the filtrate, then heated to 66° C. and stirred for 2 hours, filtered and the filtrate was concentrated under reduced pressure. Ethyl acetate (16.8 L) was added to the residue, and the mixture was stirred under reflux until the solid was dissolved. The mixture was filtered while hot, and the filtrate was allowed to slowly cool to 20° C. and then filtered. The filter cake was collected and dried to give the compound represented by formula. (I). LCMS (ESI) m/z: 525.2 [M+H]$^+$; $^1$HNMR (400 MHz, CD$_3$OD) δ ppm 8.72 (d, J=5.01 Hz, 1H), 8.52 (s, 2H), 8.38 (s, 1H), 8.24-8.33 (m, 2H), 8.06-8.15 (m, 2H), 7.46-7.57 (m, 3H), 6.49 (q, J=7.17 Hz, 1H), 4.03 (d, J=5.75 Hz, 2H), 2.95 (brd, J=11.74 Hz, 2H), 2.31 (s, 3H), 2.04-2.14 (m, 2H), 1.96 (d, J=7.09 Hz, 3H), 1.80-1.92 (m, 3H), 1.40-1.58 (m, 2H).

Preparation of the Crystal Form a of the Compound Represented by Formula (I):

The compound represented by formula (I) (850 g) was added to ethyl acetate (6.8 L), heated to reflux temperature and stirred for 2 hours. The reaction solution was slowly cooled to 35° C. and stirred for 16 hours, filtered, and the filter cake was collected and dried to give crystal form A of the compound represented by formula (I). $^1$H NMR (400 MHz, DMSO-d$_6$) δ ppm 1.23-1.40 (m, 2H), 1.65-1.78 (m, 3H), 1.79-1.89 (m, 2H), 1.91 (d, J=7.21 Hz, 3H), 2.15 (s, 3H), 2.78 (br d, J=11.25 Hz, 2H), 4.03 (d, J=5.99 Hz, 2H), 6.35 (d, J=7.09 Hz, 1H), 7.46-7.58 (m, 2H), 7.73 (dd, J=5.01, 1.22 Hz, 1H), 8.18 (dd, J=11.31, 214 Hz, 1H), 8.21-8.27 (m, 1H), 8.30 (s, 1H), 8.40 (d, J=1.34 Hz, 1H), 8.48 (s, 1H), 8.63 (s, 2H), 8.79 (d, J=5.01 Hz, 1H).

Embodiment 2: Preparation of the Crystal Form B of the Compound Represented by Formula (II)

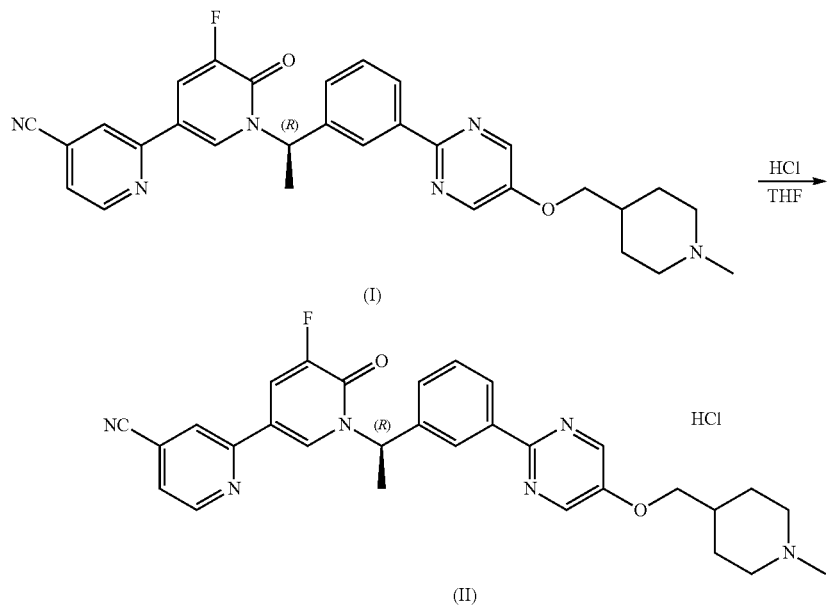

400 mg of the compound represented by formula (I) was weighted and added into a 40 mL vial, 6 mL of THF was added, the obtained sample was placed on a magnetic stirrer (40° C.) and stirred for 5 min for dissolution, and then an appropriate amount of hydrochloric acid (the molar ratio of the compound represented by formula (I) to hydrochloric acid was 1:1.05, the hydrochloric acid was added after diluted with THF) was slowly added and the phenomenon was observed. The sample was placed on a magnetic stirrer (40° C.) and was stirred overnight. A white solid precipitated from the reaction mixture. The sample solution was quickly centrifuged and the supernatant was discarded. The solid obtained was dried in a vacuum drying oven at 30° C. overnight to give the crystal form B of the compound of formula (II).

Embodiment 3: Preparation of the Crystal Form C of the Compound Represented by Formula (III)

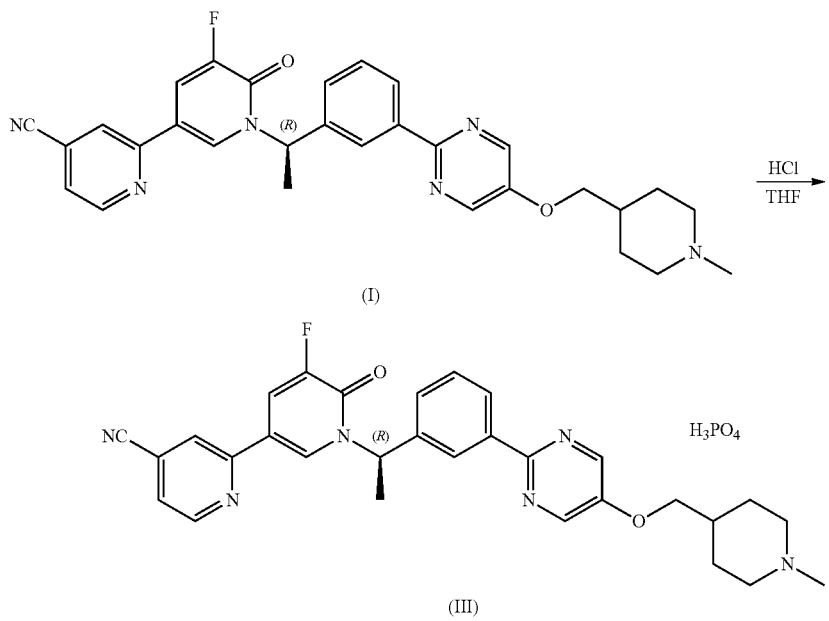

400 mg of the compound represented by formula (I) was weighted and added into a 40 mL vial, 6 mL of THF was added thereto, the sample was placed on a magnetic stirrer (40° C.) and stirred for 5 min for dissolution, and then an appropriate amount of phosphoric acid (the molar ratio of the compound represented by formula (I) to phosphoric acid was 1:1.05, the phosphoric acid was added after diluted with THF) was slowly added and the phenomenon was observed. The sample was placed on a magnetic stirrer (40° C.) and stirred overnight. A white solid precipitated from the reaction mixture. The sample solution was quickly centrifuged and the supernatant was discarded. The solid obtained was dried in a vacuum drying oven at 30° C. overnight to give the crystal form C of the compound of formula (III). $^1$HNMR. (400 MHz, DMSO-$d_6$) δ ppm 1.49 (q, J=10.88 Hz, 2H), 1.71-2.05 (m, 6H, 2.28-2.49 (m, 6H), 3.07 (brd, J=10.79 Hz, 2H), 4.06 (brd, J=6.27 Hz, 2H), 6.34 (q, J=6.94 Hz, 1H), 7.44-7.62 (m, 2H), 7.73 (dd, J=4.89, 1.13 Hz, 1H), 8.18 (dd, 0.1=11.29, 2.26 Hz, 1H), 8.21-8.27 (m, 1H), 8.29 (s, 1H), 8.40 (s, 1H), 8.47 (s, 1H), 8.64 (s, 2H), 8.78 (d, J=5.02 Hz, 1H).

Embodiment 4: Stability Test of the Crystal Form A of the Compound Represented by Formula (I)

About 10 mg of the crystal form A of the compound represented by formula (I) was weighted and placed under stability test conditions, the samples were collected and analyzed after 10 days, 1 month and 2 months. The experimental results are shown in Table 6.

TABLE 6

Stability test results of the crystal form A of the compound represented by formula (I)

| | | Relative retention time (min) | 0.93 | 0.99 | 1.05 | 1.07 | 1.39 | 1.43 | 1.48 | Total impurities |
|---|---|---|---|---|---|---|---|---|---|---|
| Impurity content (%) | 0 day | | 0.14 | | | 0.52 | | | | 0.67 |
| | 60° C. | 5 days | 0.12 | 0.13 | | 0.47 | 0.17 | | 0.1 | 0.99 |
| | | 10 days | 0.12 | 0.19 | 0.14 | 0.45 | 0.41 | 0.11 | 0.23 | 1.64 |
| | Relative humidity 92.5% | 5 days | 0.14 | | | 0.53 | | | | 0.67 |
| | | 10 days | 0.14 | | | 0.52 | | | | 0.67 |
| | Light (total illuminance = 1.2 × 106 Lux · hr/near ultraviolet = 200 w · hr/m$^2$) | | 0.11 | 0.29 | 0.8 | 0.46 | 3.98 | 1.18 | 1.62 | 13.45 |
| | 40° C. | 10 days | 0.14 | | | 0.5 | | | | 0.58 |
| | Relative humidity 75% | 1 month | 0.12 | | | 0.45 | | | | 0.63 |
| | | 2 months | 0.15 | | | 0.52 | | | | 0.66 |
| | 60° C. | 10 days | 0.14 | | | 0.53 | | | | 0.67 |
| | Relative humidity 75% | 1 month | 0.13 | | | 0.49 | | | | 0.62 |
| | | 2 months | 0.17 | | | 0.59 | | | | 0.75 |

Note:
Blank means not detected

It can be seen from the experimental results that the crystal form A of the compound represented by formula (I) has no significant change in impurity content under high temperature and high humidity conditions, and has good stability.

Embodiment 5: Stability Test of the Crystal Form B of the Compound Represented by Formula (II)

About 10 mg of the crystal form B of the compound represented by formula (II) was weighted and placed under stability test conditions, and the samples were collected and analyzed after 5 days, 10 days, and 1 month. The experimental results are shown in Table 7.

TABLE 7

Stability test results of the crystal form B of the compound represented by formula (II)

| | | Relative retention time (min) | 0.77 | 1.04 | 1.4 | 1.41 | 1.43 | 1.49 | Total impurities |
|---|---|---|---|---|---|---|---|---|---|
| Impurity content (%) | 0 day | | 0.05 | 2.18 | | | | | 2.24 |
| | 40° C. relative humidity 75% | 10 days | 0.18 | 2.02 | | | | | 2.2 |
| | | 1 month | 0.23 | 1.95 | | | | | 2.18 |
| | 60° C. relative humidity 75% | 10 days | 0.42 | 1.72 | | | | | 2.13 |
| | | 1 month | 0.36 | 1.76 | | | | | 2.12 |
| | Light (total illuminance = 1.2 × 106 Lux · hr/near ultraviolet = 200 w · hr/m$^2$) | | | | 2.22 | 0.17 | | | 2.39 |

TABLE 7-continued

Stability test results of the crystal form B of the compound represented by formula (II)

| Relative retention time (min) | | 0.77 | 1.04 | 1.4 | 1.41 | 1.43 | 1.49 | Total impurities |
|---|---|---|---|---|---|---|---|---|
| 60° C. | 5 days | 0.06 | 2.18 | 0.06 | | | | 2.3 |
| | 10 days | | 2.16 | 0.12 | | | | 2.29 |
| | 1 month | 0.05 | 2.27 | 0.28 | 0.07 | 0.06 | 0.05 | 2.78 |
| Relative | 5 days | 0.13 | 2.08 | | | | | 2.21 |
| humidity 92.5% | 10 days | 0.16 | 2.04 | | | | | 2.2 |
| | 1 month | 0.2 | 2.03 | | | | | 2.23 |

Note:
Blank means not detected

It can be seen from the experimental results that the crystal form B of the compound represented by formula (II) is stable under high temperature and light conditions.

Embodiment 6: Stability Test of the Crystal Form C of the Compound Represented by Formula (III)

About 10 mg of the crystal form C of the compound represented by formula (III) was weighted and placed under stability test conditions, and the samples were collected and analyzed after 5 days, 10 days, and 1 month respectively. The experimental results are shown in Table 8.

TABLE 8

Stability test results of the crystal form C of the compound represented by formula (III)

| | Relative retention time (min) | | 0.45 | 0.7 | 0.75 | 0.77 | 0.81 | 0.87 | 0.94 | 1.04 | 1.07 | 1.4 | Total impurities |
|---|---|---|---|---|---|---|---|---|---|---|---|---|---|
| Impurity content (%) | 0 day | | | | | 0.1 | | | 0.09 | 1.98 | 0.05 | | 2.22 |
| | 40° C. | 10 days | | | | 0.15 | | | 0.09 | 1.97 | 0.05 | | 2.26 |
| | Relative humidity 75% | 1 month | | | | 0.25 | | 0.05 | 0.09 | 1.86 | 0.06 | | 2.31 |
| | 60° C. | 10 days | | | | 4.04 | | 0.57 | 0.09 | 1.28 | | 0.07 | 6.04 |
| | Relative humidity 75% | 1 month | | | | 10.4 | | 1.36 | 0.08 | 0.61 | 0.06 | 1.23 | 12.75 |
| | Light (total illuminance = 1.2 × 106 Lux · hr/near ultraviolet = 200 w · hr/m²) | | 0.05 | 0.12 | 0.05 | 0.33 | 0.11 | | 0.24 | 2 | 0.05 | | 2.94 |
| | 60° C. | 5 days | | | | 0.09 | | | 0.09 | 2.04 | 0.05 | | 2.27 |
| | | 10 days | | | | 0.11 | | | 0.09 | 2.1 | 0.06 | | 2.35 |
| | | 1 month | | | | 0.12 | | | 0.1 | 2.03 | 0.05 | 0.07 | 2.35 |
| | Relative humidity 92.5% | 5 days | | | | 0.11 | | | 0.09 | 2.03 | 0.02 | | 2.29 |
| | | 10 days | | | | 0.13 | | | 0.09 | 1.96 | 0.05 | | 2.22 |
| | | 1 month | | | | 0.21 | | | 0.09 | 1.93 | 0.05 | | 2.28 |

Note:
Blank means not detected

It can be seen from the experimental results that the crystal form C of the compound represented by formula (III) is relatively stable under high temperature and high humidity conditions, respectively.

Embodiment 7: Study on Hygroscopicity of the Crystal Form A of the Compound Represented by Formula (I)

3 dry glass weighing bottles with stopper (outer diameter of 50 mm, height of 30 mm) were placed in a desiccator having saturated ammonium chloride solution placed at the bottom, the weighing bottles were left open, and the desiccator was covered with lid, placed in a thermostat setting at 25° C. overnight.

The weighing bottles were took out and accurately weighed, the weight data were noted as $m_1 1$, $m_1 2$ and $m_1 3$ respectively.

An appropriate amount of the crystal form A of the compound represented by formula (I), was spread in the weighed weighing bottles (the thickness of the sample was about 1 mm), and then accurately weighed, the weight data were noted as $m_2 1$, $m_2 2$ and $m_2 3$, respectively.

The open weighing bottles and the bottle stoppers were placed in a desiccator having saturated ammonium chloride solution placed at the bottom, and the desiccator was covered with a lid, placed in a thermostat setting at 25° C. for 24 hours.

After standing for 24 hours, the weighing bottles were closed with the stoppers, then accurately weighed, and the weight data were noted as $m_3 1$, $m_3 2$ and $m_3 3$.

Hygroscopicity weight gain was calculated, the calculation formula was as follows:

Percentage gain=100%×$(m_3-m_2)/(m_2-m_1)$

TABLE 9

Hygroscopicity of the crystal form A of the compound represented by formula (I)

| Sample No. | $m_1$(mg) | $m_2$(mg) | $m_3$(mg) | Percentage gain (%) | Average value (%) |
|---|---|---|---|---|---|
| 1 | 36264.06 | 37307.72 | 37308.04 | 0.03 | 0.060 |
| 2 | 33778.57 | 34860.10 | 34860.94 | 0.08 | |
| 3 | 35815.99 | 36999.50 | 37000.34 | 0.07 | |

According to the results of the hygroscopicity test, the average hygroscopicity of the crystal form A of the compound represented by formula (I) is 0.060% (<0.20%), so the crystal form A of the compound represented by formula (I) has no or almost no hygroscopicity.

Embodiment 8: Solubility Test of the Crystal Form A of the Compound Represented by Formula (I)

10 mg of the crystal form A of the compound represented by formula (I) was placed into a glass bottle, 1 mL of solvent was added thereto and the bottle was shaken vigorously for 30 seconds every 5 minutes at 25° C.±2° C., the dissolution was observed over 30 minutes. The corresponding data were recorded in the table.

For insoluble samples, another 1 mg of the crystal form A of the compound represented by formula (I) was placed into a glass bottle, an appropriate solvent was added thereto, and the bottle was shaken vigorously for 30 seconds every 5 minutes at 25° C.±2° C., the dissolution was observed over 30 minutes. The corresponding data were recorded in Table 10.

TABLE 10

The solubility of the crystal form A of the compound represented by formula (I) in different solvents

| Solvent | Solubility classification | Solvent | Solubility classification |
|---|---|---|---|
| water | Very soluble | acetone | Slightly soluble |
| Tetrahydrofuran | Sparingly soluble | 0.1N HCl | Soluble |
| Ethyl acetate | Very slightly soluble | 0.1N NaOH | Practically insoluble or insoluble |
| Acetonitrile | Very slightly soluble | Trifluoroacetic acid | Sparingly soluble |
| n-Hexane | Practically insoluble or insoluble | Ethanol | Very slightly soluble |
| Diethylamine | Practically insoluble or insoluble | N-Methylpyrrolidone | Very soluble |

It can be seen from the experimental results that the crystal form A of the compound represented by formula (I) is very soluble in water or N-methylpyrrolidone, soluble in 0.1 N HCl, sparingly soluble in tetrahydrofuran or trifluoroacetic acid, and very slightly soluble in ethyl acetate, acetonitrile or ethanol; practically insoluble or insoluble in n-hexane, diethylamine or 0.1 N sodium hydroxide solution.

Embodiment 9: Enzymatic Activity Test of Crystal Form A of the Compound Represented by Formula (I)

Reagents and Consumables:
cMET (invitrogen PV3143)
Tracer 236 (Lot Number: 10815978)
Eu-Anti-His AB (MAb Anti 6HIS-K)
PerkinElmer corporation Envison detection 665 nm and 615 nm
384-well plate_checkerboard (PerkinElmer #6007299)

Experimental Principle:
The present experiment utilized the LanthaScreen™ Eu Kinase Binding Assay, as shown in FIG. 1, detection of Alexa Fluor conjugates or kinase combines tracer agent was done by adding Eu labelled antibody. The binding of tracer agent and antibody and kinase leaded to high FRET standard, while using kinase inhibitor instead of tracer agent would lead to loss of FRET.

Experimental Method:
1) The antibody Eu-Anti-His AB, enzyme cMET, tracer agent Tracer236 were diluted.
2) Preparation of the compound: 10 mM test compound and reference compound were diluted with 100% DMSO to 0.667 mM, then fully automated microplate pretreatment system ECHO was used for a 3-fold dilution with 8 concentration gradients. Double duplicate wells were set and each of them 75 nL.
3) The mixture of 7.5 μL: antibody (1/375 nM) and kinase (10 nM) was added to the compound plate, followed by addition of 7.5 Tracer (60 nM). Final concentration: cMET: 5 nM, Tracer 236: 30 nM, Eu-Anti-His AB (MAb Anti 6HIS-K): 1/750 nM.
4) After 60 minutes of incubation at 4° C., the plates were read with a multi-labelled microplate reader Envision (data analysis of 665 nm/615 mm signal values with Prism 5; Ex excitation light: Laser mirror 446, Em excitation light; 615 and 665 nM.

Experimental Result: See Table 11.

TABLE 11

The $IC_{50}$ value of the compound represented by formula (I) on the inhibition of kinase activity

| Test compound | c-MET $IC_{50}$(nM) |
|---|---|
| The compound represented by formula (I) | 1.09 |

The experimental result shows that the compound represented by formula (I) has strong inhibitory activity on c-MET enzyme.

Embodiment 10: Cell Proliferation Inhibition Experiment of the Compound Represented by Formula (I)

The present experiment intends to study the inhibitory effect of the compound represented by formula (I) on prostate cancer cell LNCaP overexpressing AKT.

Reagents and Consumables:
1) Cell culture: DMFM cell medium, fetal bovine serum, DPBS
2) Cell line: MHCC97-H
3) Detection reagent: live cell detection kit CellTiter-Glo
4) Other major consumables and reagents: compound dilution plate, intermediate plate, test plate, DMSO Experimental Method:

1. Preparation of the Cell Plates

MHCC97-H cells were seeded separately into 384-well plates with each of the well containing 500 cells. The cell plates were placed and incubated in a carbon dioxide incubator overnight.

2. Preparation of the Compound.

Echo was used for 4-fold dilution and 9 concentrations were prepared, ready for double duplicate wells assay.

3. Treatment of Cells with the Compound

The compound was transferred to the cell plates at a starting concentration of 10 µM. The cell plates were incubated in a carbon dioxide incubator for 3 days.

4. Detection

The Promegaer Cell Titer-Glo reagent was added into the cell plates and the plates were incubated at room temperature for 10 minutes until the luminescence signal was stable. The plates were read with a PerkinElmer Envision multi-label analyzer.

Experimental Results: See Table 12:

TABLE 12

The $IC_{50}$ value of the compound represented by formula (I) on cell proliferation inhibition

| Cell name | $IC_{50}$ (nM) The compound represented by formula (I) |
| --- | --- |
| MHCC97H | 8.80 |

The result of the experiment shows that the compound represented by formula (I) has good inhibitory activity on MHCC97H cell.

Embodiment 11: In Vivo Efficacy Study of the Compound Represented by Formula (I)

Cell Culture:

MHCC97H cells were cultured in a single layer in-vitro. The culturing condition was RPMI1640 medium supplemented with 10% heat-inactivated fetal bovine serum, 1% penicillin-streptomycin double antibody under 37° C., 5% carbon dioxide. Digestion and passage treatment with trypsin-EDTA was done twice a week. When the cells were in the exponential growing phase, the cells were collected, counted and inoculated.

Animal:

BALB/c nude mice, male. 6-8 weeks old, weighting 18-22 g.

Tumor Inoculation:

0.2 mL of a cell suspension containing 5×10^6 MHCC97H was subcutaneously inoculated into the right back of each mouse. Drugs were administered by group after the average tumor volume reached approximately 172 mm³. The experimental grouping and dosage regimen are shown in the table below.

Aim of the Assay

Investigation of whether the tumor growth was inhibited, delayed or cured. The diameters of the tumor were measured twice a week using a vernier caliper. The formula for calculating the tumor volume is $V=0.5a \times b^2$, and a and b represent the long and short diameters of the tumor respectively. The antitumor effect (TGI) of the compound was evaluated by T-C (days) and T/C (%).

Experimental Result: See Table 13.

TABLE 13

Evaluation of anti-tumor efficacy of test drug on human liver cancer MHCC97H cell xenograft tumor model (Calculated based on the tumor volume on the 24th day after administration)

| Grouping | tumor volume (mm³)[a] (24th day) | T/C (%) | TGI (%) | p value [b] |
| --- | --- | --- | --- | --- |
| blank | 2059 ± 305 | — | — | — |
| Tepotinib | 255 ± 5 | 12.4 | 95.6 | <0.001 |
| Compound represented by formula (I) | 153 ± 12 | 7.4 | 101.0 | <0.001 |

Remark: a. average value±SEM; b. p value was calculated based on the tumor volume.

Conclusion: The compound represented by formula (I) shows better tumor inhibitory effect than tepotinib in the pharmacodynamic experiment on MHCC97H liver cancer cell subcutaneous xenograft tumor model.

The compound represented by formula (I) has better metabolic stability than tepotinib. The $t_{1/2}$ of the compound represented by formula (I) by human, rat, and mouse liver microsome metabolism were 62.1 min, 36.5 min, and 49.1 min, respectively, under the same conditions, the $t_{1/2}$ of tepotinib by human, rat and mouse liver microsome metabolism was 48.3 min, 10.5 min, and 12.4 min, respectively. The compound represented by the present disclosure has increased half-life, thus having prolonged action time against the target, enhanced metabolism stability and better inhibitory activity. The prolongation of half-life will allow the drug concentration to be maintained in the blood for a longer period of time. From this, it can be predicted that the compound will reduce the dose or the frequency of administration compared with similar drugs when used in tumor treatment, and patient compliance will be significantly improved.

When c-MET binds to HGF, the MAPK, PI3K/AKT, Cdc42/Rac1 and other pathways will be activated, leading to tumor cell survival and proliferation, thereby accelerating the tumor growth. Therefore, the pyridone compounds as c-Met inhibitor have great application prospects in targeted therapy drugs such as liver cancer, non-small cell lung cancer and gastric cancer. Especially in the treatment of liver cancer, these compounds have a precise therapeutic effect on liver cancer with high expression of c-MET. Therefore, the compound represented by formula (I) as pyridone c-MET inhibitor is expected to be a more therapeutically effective new drug than other similar products in view of its remarkable inhibitory activity in vivo and in vitro, as well as its good metabolic stability.

What is claimed is:

1. A crystal form A of a compound represented by formula (I), wherein the X-ray powder diffraction pattern of the crystal form A comprises characteristic diffraction peaks at the following angle 2θ: 4.54°±0.2°, 13.70°±0.2°, 17.84±0.2°, 21.24°±0.2° and 26.62±0.2°;

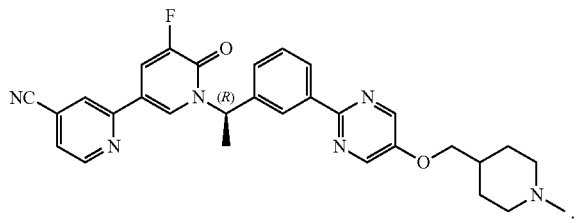

2. The crystal form A as defined in claim 1, wherein the X-ray powder diffraction pattern of the crystal form A comprises characteristic diffraction peaks at the following angle 2θ: 4.54°±0.2°, 13.70°±0.2°, 15.14±0.2°, 17.84±0.2°, 18.40°±0.2°, 21.24°±0.2°, 24.06°±0.2°, 26.62±0.2° and 27.44±0.2°;

or, the differential scanning calorimetry curve of the crystal form A has an endothermic peak with an onset temperature at 171.90° C.±3° C.;

or, the thermogravimetric analysis curve of the crystal form A shows a weight loss of 0.1870% occurred at 223.23° C.±3° C., and a weight loss of 10.22% occurred at 305.06° C.±3° C.

Figure 2:
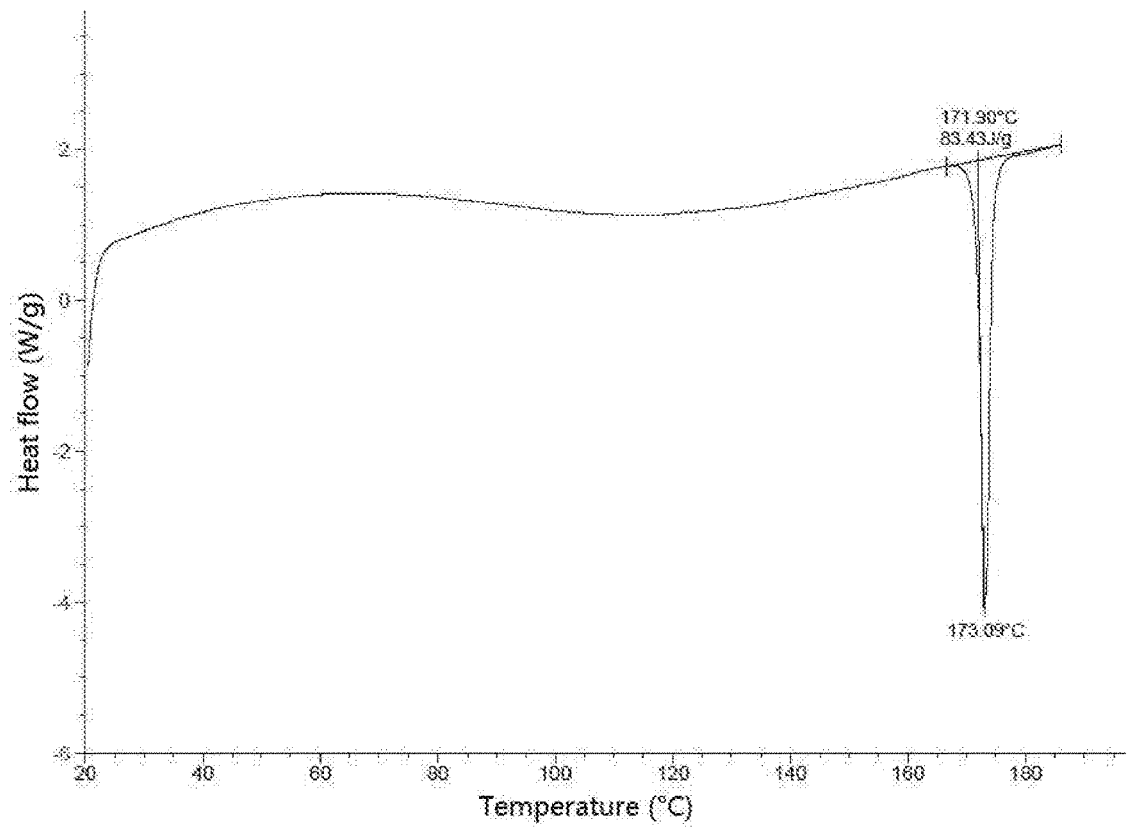
FIG. 2 is the DSC spectrum of the crystal form A of the compound represented by formula (I).
Figure 3:
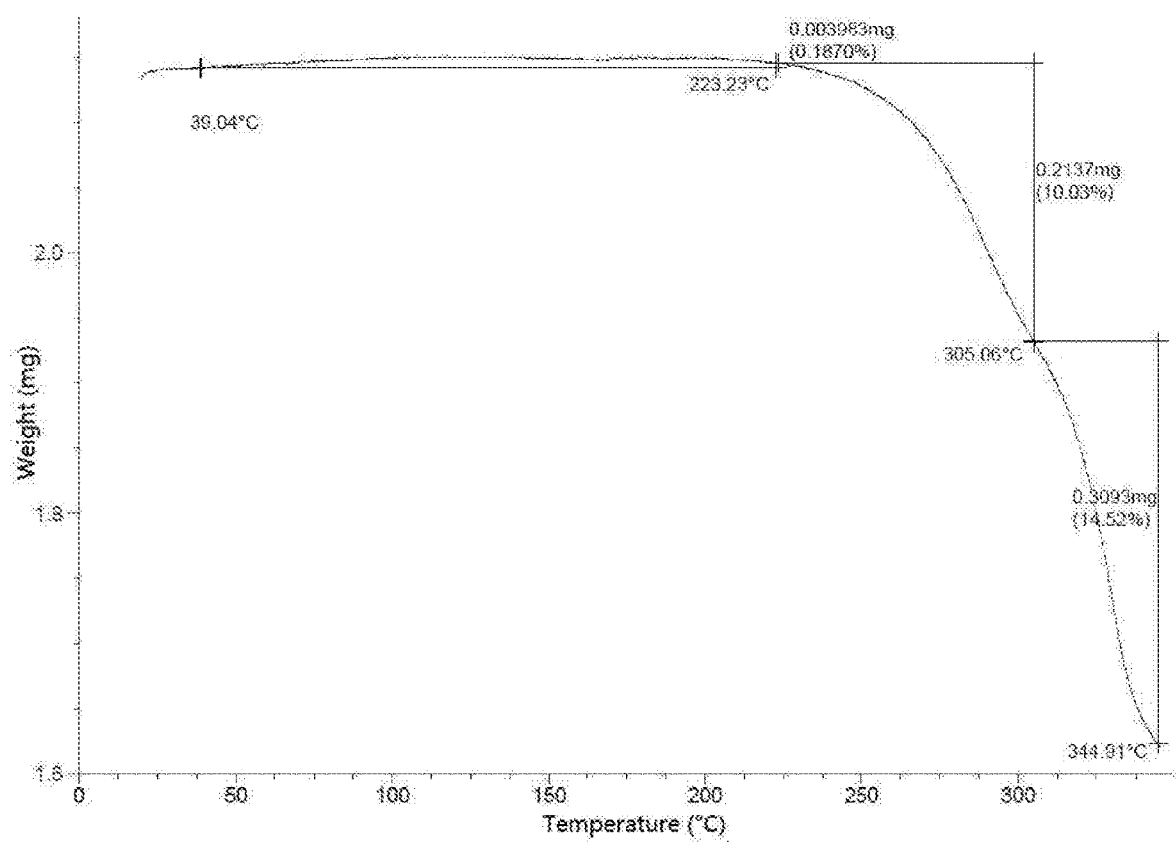
FIG. 3 is the TGA spectrum of the crystal form A of the compound represented by formula (I).
Figure 4:
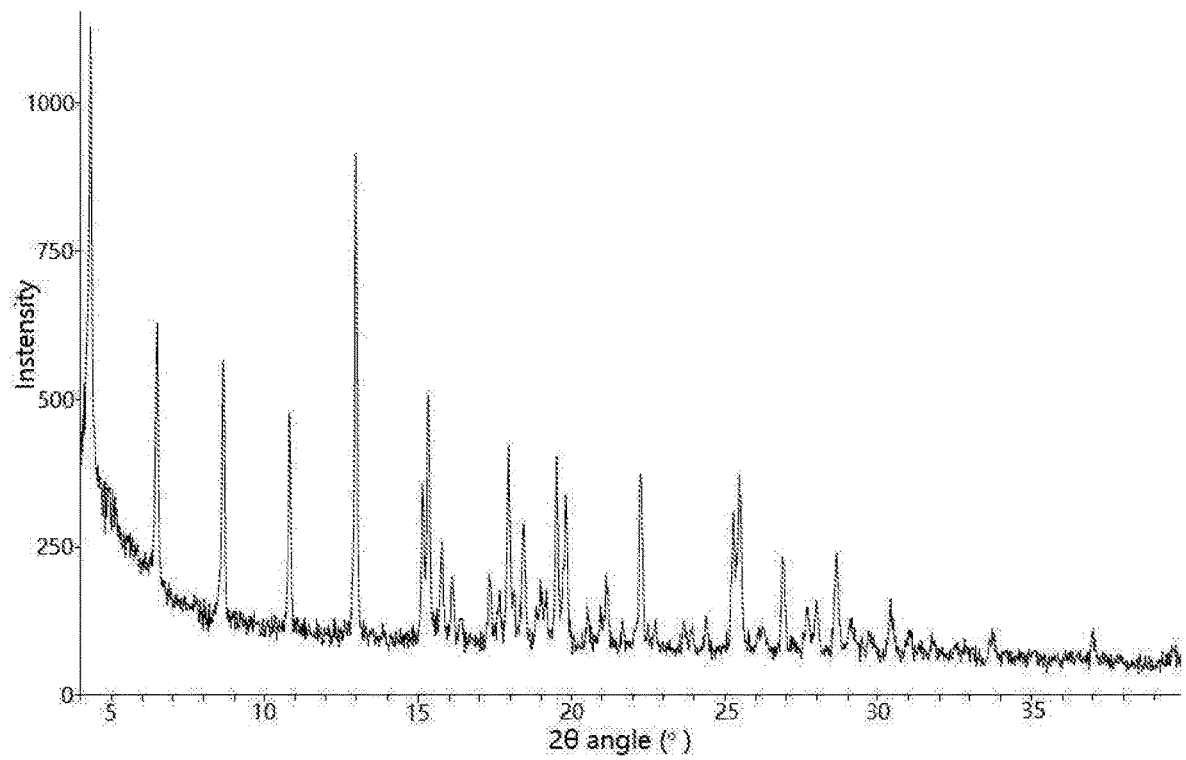
FIG. 4 is the XRPD spectrum of the crystal form B of the compound represented by formula (II).

3. The crystal form A as defined in claim 1, wherein the X-ray powder diffraction pattern of the crystal form A comprises characteristic diffraction peaks at the following angle 2θ: 4.538°, 9.021°, 11.300°, 13.699°, 15.141°, 16.640°, 17.840°, 18.399°, 19.039°, 19.620°, 20.441°, 21.241°, 22.598°, 24.060°, 24.962°, 25.660°, 26.621°, 27.440°, 28.258°, 29.159°, 31.081°, 32.465°, 34.780°, 35.400°, 36.920° and 38.760°;

or, the differential scanning calorimetry curve of the crystal form A is as shown in FIG. 2;

or, the thermogravimetric analysis curve of the crystal form A is as shown in FIG. 3.

4. A compound represented by formula (II):

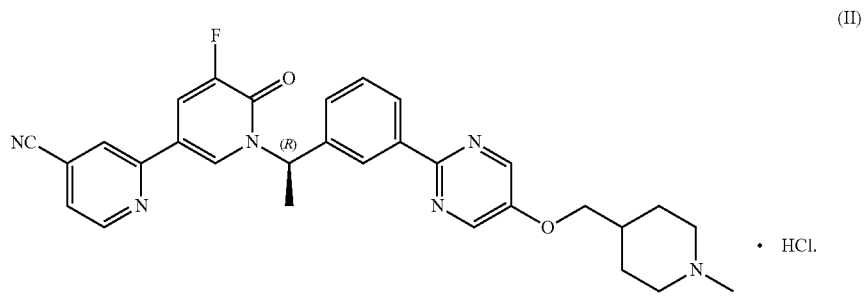

5. A crystal form B of the compound represented by formula (II) as defined in claim 4, wherein the X-ray powder diffraction pattern of the crystal form B comprises characteristic diffraction peaks at the following angle 2θ: 4.34°±0.2°, 12.99°±0.2°, 15.35°±0.2° and 25.50°±0.2°;

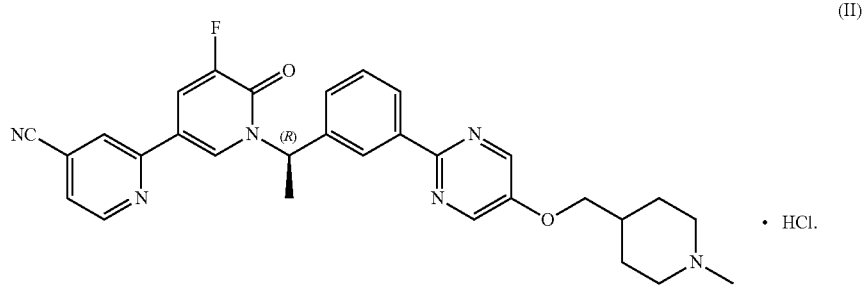

6. The crystal form B as defined in claim 5, wherein the X-ray powder diffraction pattern of the crystal form B comprises characteristic diffraction peaks at the following angle 2θ: 4.34°±0.2°, 6.50°±0.2°, 8.65°±0.2°, 10.82°±0.2°, 12.99°±0.2°, 15.35°±0.2°, 17.96°±0.2° and 25.50°±0.2°;

or, the differential scanning calorimetry curve of the crystal form B has endothermic peaks with an onset temperature at 43.98° C.±3° C. and 219.64° C.±3° C.;

or, the thermogravimetric analysis curve of the crystal form B shows a weight loss of 0.5270% occurred at 73.64° C.±3° C., and a weight loss of 1.542% occurred at 230.90° C.±3° C.

Figure 5:
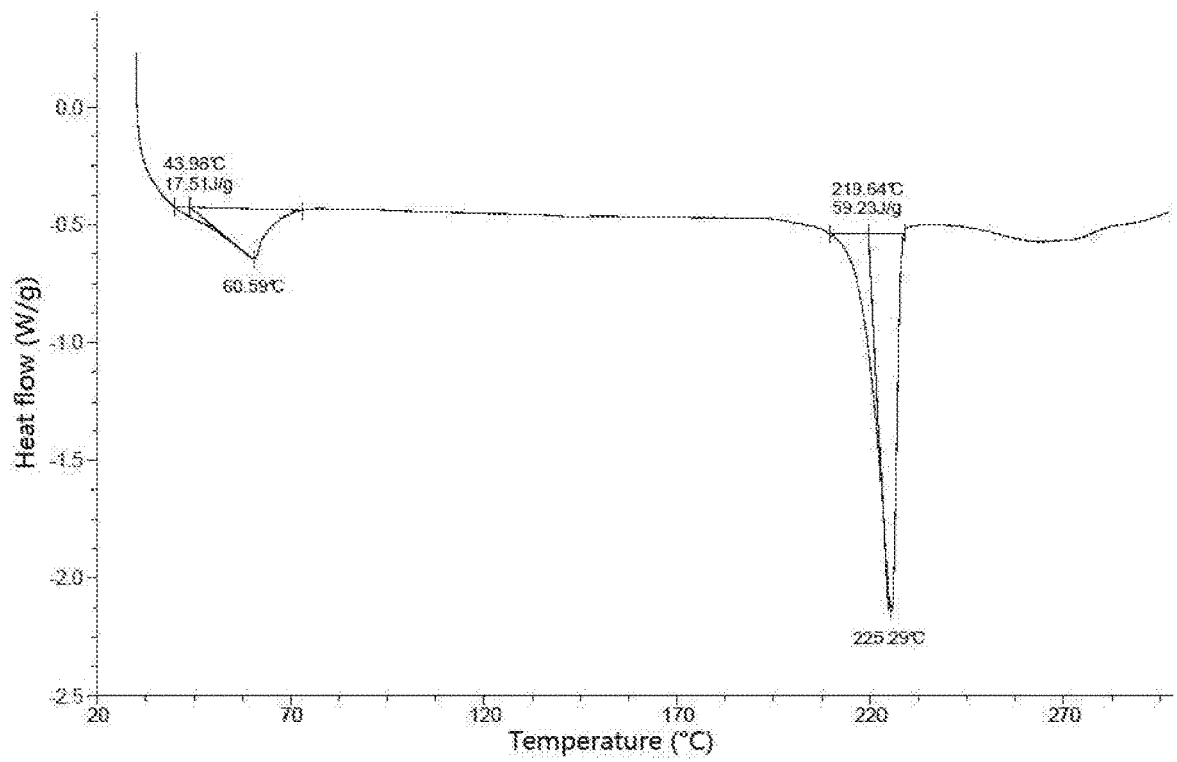
FIG. 5 is the DSC spectrum of the crystal form B of the compound represented by formula (II).
Figure 6:
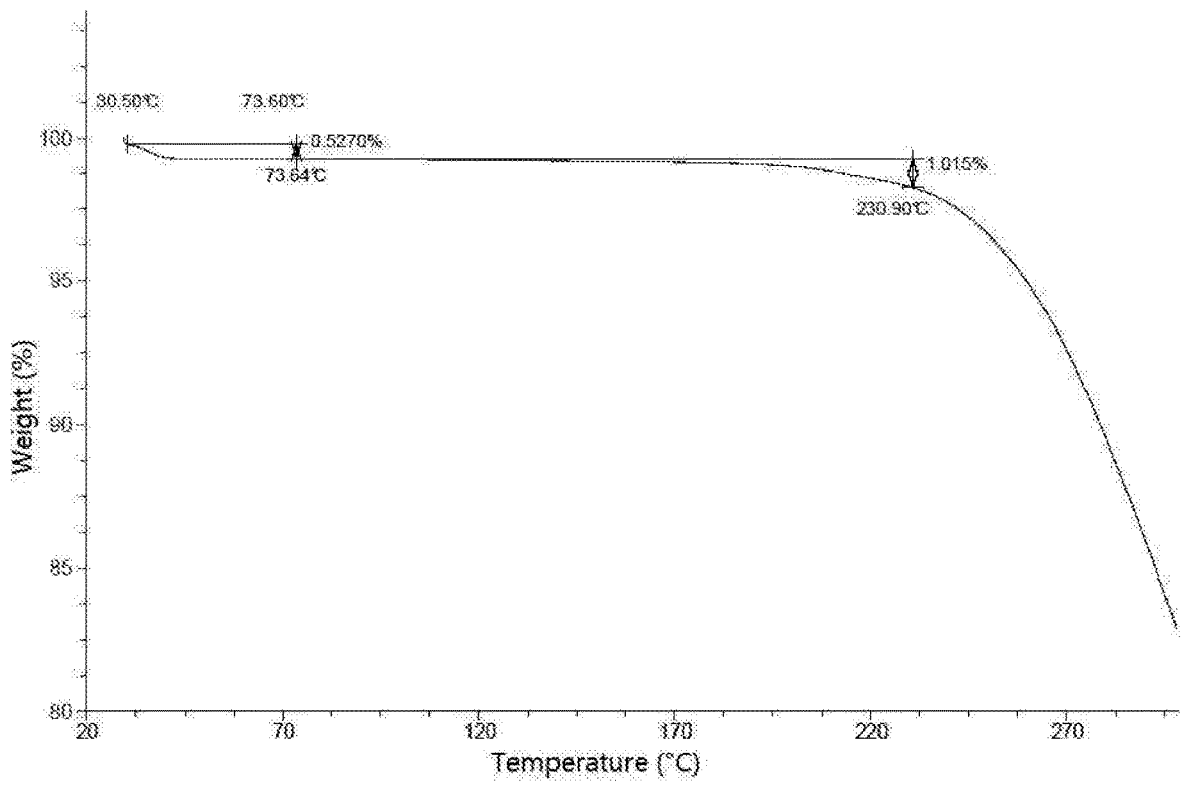
FIG. 6 is the TGA spectrum of the crystal form B of the compound represented by formula (II).
Figure 7:
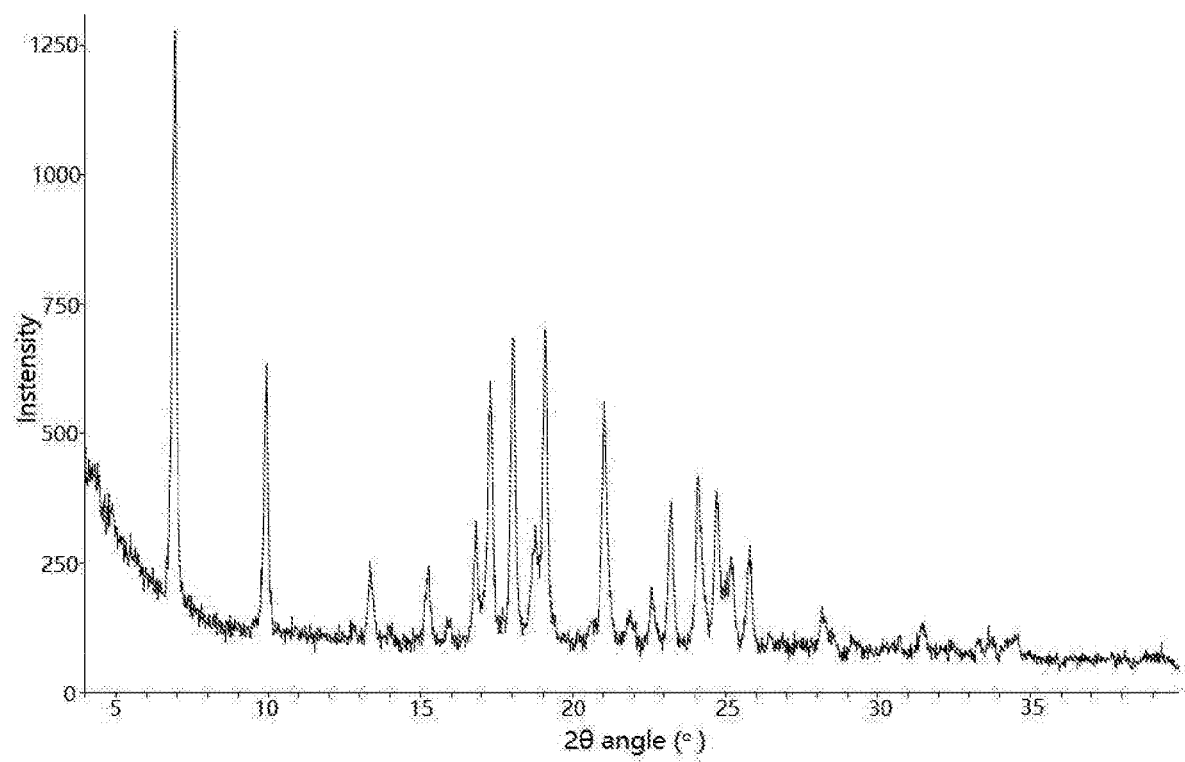
FIG. 7 is the XRPD spectrum of the crystal form C of the compound represented by formula (III).

7. The crystal form B as defined in claim 5, wherein the X-ray powder diffraction pattern of the crystal form B comprises characteristic diffraction peaks at the following angle 2θ: 4.335°, 6.502°, 8.645°, 10.816°, 12.986°, 15.349°, 15.782°, 16.109°, 17.955°, 18.447°, 19.057°, 19.534°, 19.816°, 20.531°, 21.16°, 22.265°, 22.752°, 23.907°, 24.407°, 25.499°, 26.248°, 26.886°, 27.725°, 28.004°, 28.653°, 29.127°, 29.779°, 30.432°, 31.064°, 33.734° and 37.02°;

or, the differential scanning calorimetry curve of the crystal form B is as shown in FIG. 5;

or, the thermogravimetric analysis curve of the crystal form B is as shown in FIG. 6.

8. A compound represented by formula (III):

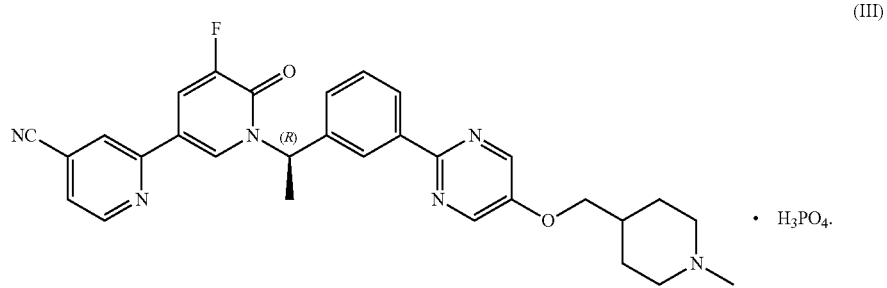

(III)

9. A crystal form C of the compound represented by formula (III) as defined in claim 8, wherein the X-ray powder diffraction pattern of the crystal form C comprises characteristic diffraction peaks at the following angle 2θ: 6.94°±0.2°, 19.08°±0.2°, 21.05°±0.2° and 24.73°±0.2°;

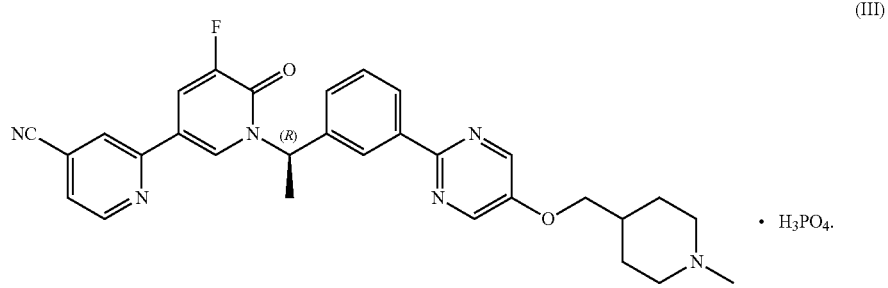

(III)

10. The crystal form C as defined in claim 9, wherein the X-ray powder diffraction pattern of the crystal form C comprises characteristic diffraction peaks at the following angle 2θ: 6.94°±0.2°, 9.94°±0.2°, 17.29°±0.2°, 18.04°±0.2°, 19.08°±0.2°, 21.05°±0.2°, 24.12°±0.2° and 24.73°±0.2°;
or, the differential scanning calorimetry curve of the crystal form C has an endothermic peak with an onset temperature at 198.16° C.±3° C.;
or, the thermogravimetric analysis curve of the crystal form C shows a weight loss of 0.4541% occurred at 204.73° C.±3° C.

Figure 8:
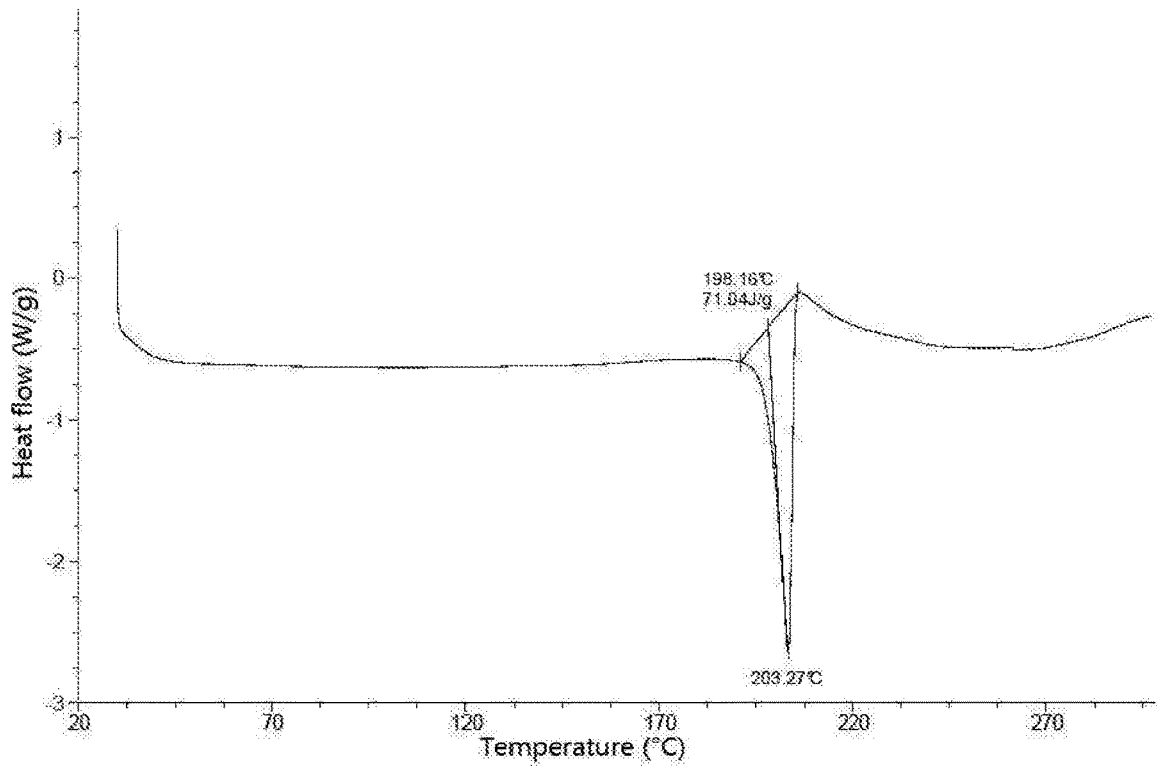
FIG. 8 is the DSC spectrum of the crystal form C of the compound represented by formula (III).
Figure 9:
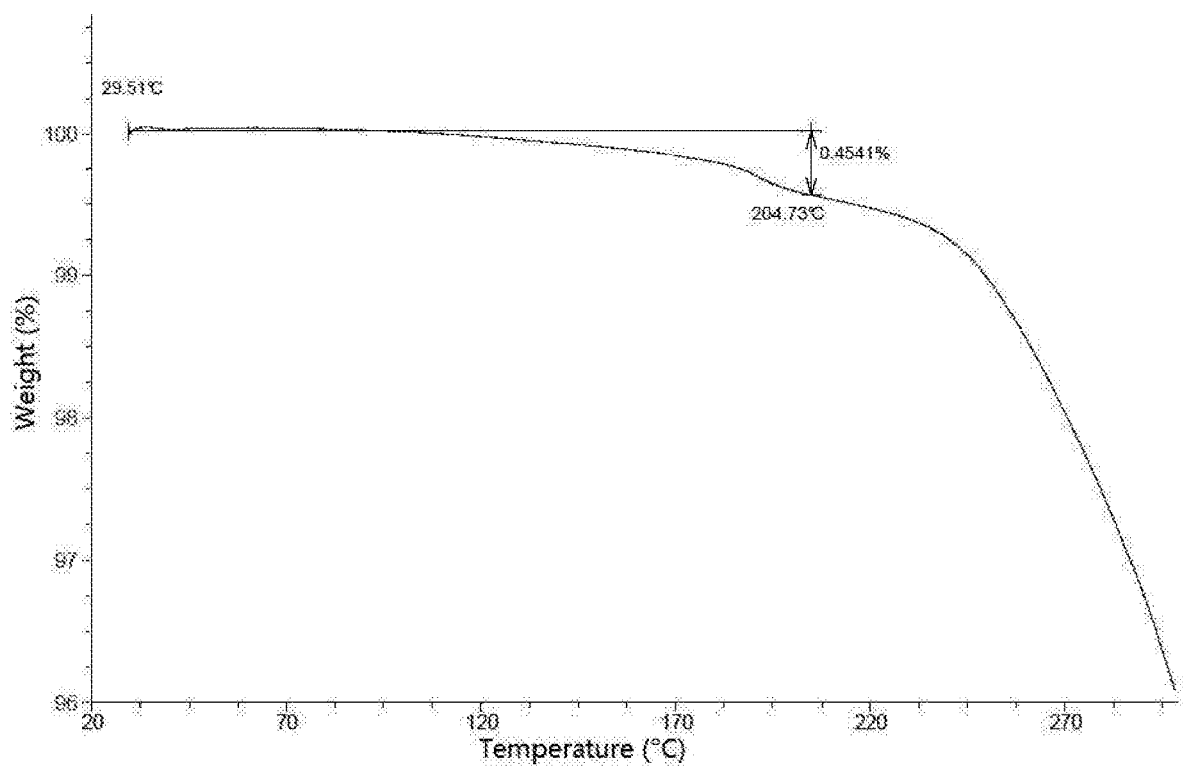
FIG. 9 is the TGA spectrum of the crystal form C of the compound represented by formula (III).

11. The crystal form C as defined in claim 9, wherein the X-ray powder diffraction pattern of the crystal form C comprises characteristic diffraction peaks at the following angle 2θ: 6.94°, 9.94°, 13.36°, 15.271°, 16.83°, 17.286°, 18.038°, 18.767°, 19.082°, 20.605°, 21.054°, 21.884°, 22.615°, 23.228°, 24.118°, 24.728°, 25.182°, 25.813°, 28.182°, 30.757°, 31.498°, 33.318°, 33.77° and 34.595°;
or, the differential scanning calorimetry curve of the crystal form C is as shown in FIG. 8;
or, the thermogravimetric analysis curve of the crystal form C is as shown in FIG. 9.

12. A method for treating liver cancer in a subject in need thereof, comprising administering a therapeutically effective amount of the crystal form A as defined in claim 1 to the subject.

13. A method for treating liver cancer in a subject in need thereof, comprising administering a therapeutically effective amount of the compound as defined in claim 4 to the subject.

14. A method for treating liver cancer in a subject in need thereof, comprising administering a therapeutically effective amount of the crystal form B as defined in claim 5 to the subject.

15. A method for treating liver cancer in a subject in need thereof, comprising administering a therapeutically effective amount of the compound as defined in claim 8 to the subject.

16. A method for treating liver cancer in a subject in need thereof, comprising administering a therapeutically effective amount of the crystal form C as defined in claim 9 to the subject.

* * * * *